(12) United States Patent
Chao et al.

(10) Patent No.: US 8,455,530 B2
(45) Date of Patent: Jun. 4, 2013

(54) CRYSTALLINE FORM OF AN ALKOXYIMIDAZOL-1-YLMETHYL BIPHENYL CARBOXYLIC ACID

(75) Inventors: Robert S. Chao, Santa Clara, CA (US); Weijiang Zhang, Concord, CA (US)

(73) Assignee: Theravance, Inc., South San Francisco, CA (US)

(*) Notice: Subject to any disclaimer, the term of this patent is extended or adjusted under 35 U.S.C. 154(b) by 0 days.

(21) Appl. No.: 13/411,319

(22) Filed: Mar. 2, 2012

(65) Prior Publication Data
US 2012/0309805 A1     Dec. 6, 2012

Related U.S. Application Data

(63) Continuation of application No. 12/944,041, filed on Nov. 11, 2010, now Pat. No. 8,153,675, which is a continuation of application No. 12/569,058, filed on Sep. 29, 2009, now Pat. No. 7,855,221.

(60) Provisional application No. 61/194,762, filed on Sep. 30, 2008.

(51) Int. Cl.
*A61K 31/415*     (2006.01)
*C07D 233/54*     (2006.01)

(52) U.S. Cl.
USPC ........................ 514/398; 548/325.5

(58) Field of Classification Search
USPC ........................ 514/398; 548/325.5
See application file for complete search history.

(56) References Cited

U.S. PATENT DOCUMENTS

| | | |
|---|---|---|
| 5,444,081 A | 8/1995 | Gleason et al. |
| 2004/0048911 A1 | 3/2004 | Reitz et al. |
| 2008/0269305 A1 | 10/2008 | Allegretti et al. |
| 2009/0023228 A1 | 1/2009 | Allegretti et al. |
| 2011/0218224 A1 | 9/2011 | Fatheree |

OTHER PUBLICATIONS

International Search Report for PCT/US2009/058803 dated Mar. 1, 2010.

*Primary Examiner* — Samantha Shterengarts
(74) *Attorney, Agent, or Firm* — Jeffrey A. Hagenah; Shelley Eberle

(57) ABSTRACT

The invention provides a crystalline freebase form of 4'-{2-ethoxy-4-ethyl-5-[((S)-2-mercapto-4-methylpentanoylamino)methyl]imidazol-1-ylmethyl}-3'-fluorobiphenyl-2-carboxylic acid. This invention also provides pharmaceutical compositions comprising the crystalline compound, processes and intermediates for preparing the crystalline compound, and methods of using the crystalline compound to treat diseases such as hypertension.

6 Claims, 6 Drawing Sheets

CRYSTALLINE FORM OF AN ALKOXYIMIDAZOL-1-YLMETHYL BIPHENYL CARBOXYLIC ACID

CROSS-REFERENCE TO RELATED APPLICATIONS

This application is a continuation of Ser. No. 12/944,041, filed on Nov. 11, 2010, now allowed, which in turn is a continuation of U.S. Ser. No. 12/569,058, filed Sep. 29, 2009, now issued as U.S. Pat. No. 7,855,221, which claims the benefit of U.S. Provisional Application No. 61/194,762, filed on Sep. 30, 2008; the entire disclosures of which are incorporated herein by reference in their entirety.

BACKGROUND OF THE INVENTION

1. Field of the Invention

The present invention relates to a novel crystalline form of an alkoxyimidazol-1-ylmethyl biphenyl carboxylic acid, which has angiotensin II type 1 receptor antagonist activity and neprilysin-inhibition activity. This invention also relates to pharmaceutical compositions comprising the crystalline compound or prepared from such compound, processes and intermediates for preparing the crystalline compound, and methods of using such compound to treat diseases such as hypertension.

2. State of the Art

Commonly-assigned U.S. Publication Nos. 2008/0269305 and 2009/0023228, both to Allegretti et al. filed on Apr. 23, 2008, disclose novel compounds that possess $AT_1$ receptor antagonist activity and neprilysin (NEP) enzyme inhibition activity, the disclosures of which are incorporated herein by reference. In particular, the compound, 4'-{2-ethoxy-4-ethyl-5-[((S)-2-mercapto-4-methylpentanoylamino)methyl]imidazol-1-ylmethyl}-3'-fluorobiphenyl-2-carboxylic acid is specifically disclosed in these applications.

The chemical structure of 4'-{2-ethoxy-4-ethyl-5-[((S)-2-mercapto-4-methylpentanoylamino)methyl]imidazol-1-ylmethyl}-3'-fluorobiphenyl-2-carboxylic acid is represented by formula I:

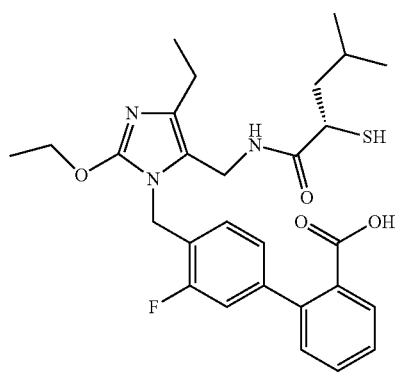

(I)

When preparing compounds for long term storage and when preparing pharmaceutical compositions and formulations, it is often desirable to have a crystalline form of the therapeutic agent that is neither hygroscopic nor deliquescent. It is also advantageous to have a crystalline form that has a relatively high melting point (i.e. greater than about 150° C.), which allows the material to be processed, for example, micronized, without significant decomposition.

No crystalline forms of the compound for formula I have been reported previously. Accordingly, a need exists for a stable, non-deliquescent form of the compound of formula I which has an acceptable level of hygroscopicity and a relatively high melting point.

SUMMARY OF THE INVENTION

The present invention relates to a crystalline form of 4'-{2-ethoxy-4-ethyl-5-[((S)-2-mercapto-4-methylpentanoylamino)methyl]imidazol-1-ylmethyl}-3'-fluorobiphenyl-2-carboxylic acid.

One aspect of the invention relates to processes for preparing a crystalline form of the compound of formula I. In one embodiment, a process for preparing a crystalline form of 4'-{2-ethoxy-4-ethyl-5-[((S)-2-mercapto-4-methylpentanoylamino)methyl]imidazol-1-ylmethyl}-3'-fluorobiphenyl-2-carboxylic acid comprises contacting 4'-{2-ethoxy-4-ethyl-5-[(S)-2-mercapto-4-methylpentanoylamino)methyl]imidazol-1-ylmethyl}-3'-fluorobiphenyl-2-carboxylic acid with an inert diluent to form a mixture; heating the mixture to between about 25° C. to about 50° C.; and cooling the mixture to form the crystalline form.

Another aspect of the invention relates to a process for purifying 4'-{2-ethoxy-4-ethyl-5-[((S)-2-mercapto-4-methylpentanoylamino)methyl]imidazol-1-ylmethyl}-3'-fluorobiphenyl-2-carboxylic acid. In one embodiment, this process comprises forming a crystalline form of 4'-{2-ethoxy-4-ethyl-5-[((S)-2-mercapto-4-methylpentanoylamino)-methyl]imidazol-1-ylmethyl}-3'-fluorobiphenyl-2-carboxylic acid. The invention also relates to products prepared by the processes described herein.

One aspect of the invention relates to a pharmaceutical composition comprising a pharmaceutically acceptable carrier and a crystalline form of 4'-{2-ethoxy-4-ethyl-5-[((S)-2-mercapto-4-methylpentanoylamino)methyl]imidazol-1-ylmethyl}-3'-fluorobiphenyl-2-carboxylic acid.

Another aspect of the invention relates to compositions comprising a crystalline form of the compound of formula I in combination with one or more other therapeutic agents. Accordingly, in one embodiment, the invention relates to a composition comprising (a) a pharmaceutically acceptable carrier and a therapeutically effective amount of a crystalline form of the compound of formula I; and (b) a therapeutically effective amount of an agent selected from diuretics, $\beta_1$ adrenergic receptor blockers, calcium channel blockers, angiotensin-converting enzyme inhibitors, $AT_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, vasopressin receptor antagonists, and combinations thereof; wherein the crystalline form and the agent are formulated together or separately. When the agent is formulated separately, a pharmaceutically acceptable carrier may be included.

Yet another aspect of the invention relates to a method for treating hypertension or heart failure, comprising administering to a patient in need of treatment a therapeutically effective amount of a crystalline form of 4'-{2-ethoxy-4-ethyl-5-[((S)-2-mercapto-4-methylpentanoylamino)methyl]imidazol-1-ylmethyl}-3'-fluorobiphenyl-2-carboxylic acid.

The invention also relates to the use of a crystalline form of 4'-{2-ethoxy-4-ethyl-5-[((S)-2-mercapto-4-methylpentanoylamino)methyl]imidazol-1-ylmethyl}-3'-fluorobiphenyl-2-carboxylic acid for the manufacture of a medicament.

Additionally, the invention relates to the use of a crystalline form of 4'-{2-ethoxy-4-ethyl-5-[((S)-2-mercapto-4-methylpentanoylamino)methyl]imidazol-1-ylmethyl}-3'-fluorobiphenyl-2-carboxylic acid for the manufacture of a medicament; especially for the manufacture of a medicament for the treatment of hypertension or heart failure.

BRIEF DESCRIPTION OF THE DRAWINGS

Various aspects of the present invention are illustrated by reference to the accompanying drawings.

DETAILED DESCRIPTION OF THE INVENTION

Figure 1:
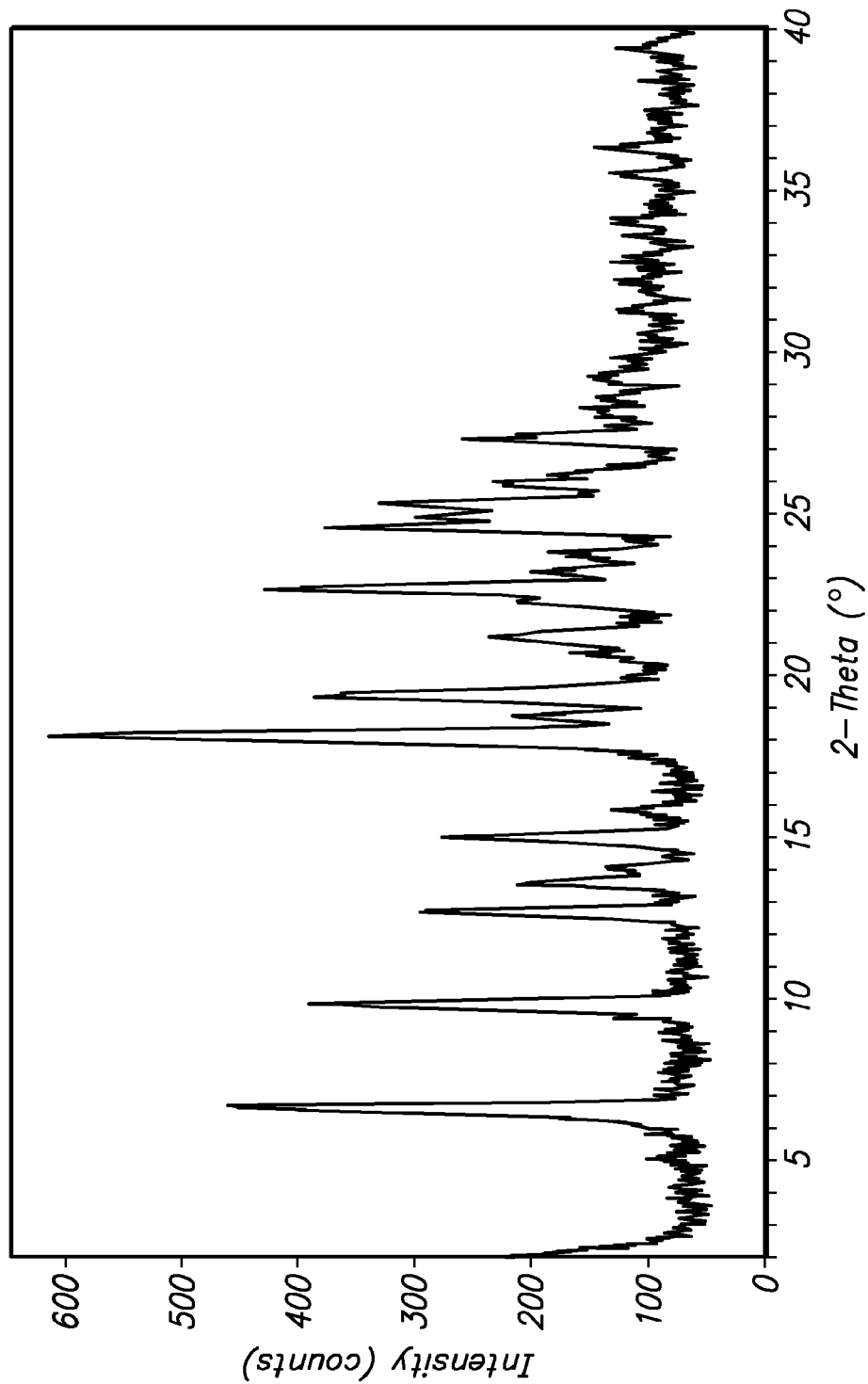
FIG. 1 shows a powder x-ray diffraction (PXRD) pattern of the crystalline form of the compound of formula I.

This invention provides a crystalline form of 4'-{2-ethoxy-4-ethyl-5-[((S)-2-mercapto-4-methylpentanoylamino)methyl]imidazol-1-ylmethyl}-3'-fluorobiphenyl-2-carboxylic acid. This crystalline form is not associated with any counterions and is referred to herein as a freebase crystalline form.

The active agent (i.e., the compound of formula I) contains one chiral center having the (S) configuration. However, it will be understood by those skilled in the art that minor amounts of the (R) stereoisomer may be present in the compositions of the invention unless otherwise indicated, provided that the utility of the composition as a whole is not eliminated by the presence of such an isomer. In addition, since the compound of formula I contains both a basic moiety (imidazole), and an acidic moiety (carboxylic acid), it may exist as a zwitterion.

The present invention provides a crystalline form of 4'-{2-ethoxy-4-ethyl-5-[((S)-2-mercapto-4-methylpentanoylamino)methyl]imidazol-1-ylmethyl}-3'-fluorobiphenyl-2-carboxylic acid. Surprisingly, this crystalline form has been found not to be deliquescent, even when exposed to atmospheric moisture. Additionally, the crystalline compound of the invention has an acceptable level of hygroscopicity and a high melting point.

The compound of formula I has $AT_1$ receptor antagonist activity and NEP inhibition activity. The crystalline form of the compound of formula I is expected to have the same activity, and thus the same utility in treating diseases such as hypertension and heart failure. Therefore, among other uses, the crystalline form of the compound of formula I is useful for preparing pharmaceutical compositions for treating hypertension or heart failure.

The compound of formula I has been named using the commercially-available AutoNom software (MDL, San Leandro, Calif.).

DEFINITIONS

When describing the compounds, compositions, methods and processes of the invention, the following terms have the following meanings unless otherwise indicated. Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

As used herein, the phrase "having the formula" or "having the structure" is not intended to be limiting and is used in the same way that the term "comprising" is commonly used.

The term "melting point" as used herein means the temperature at which the maximum endothermic heat flow is observed by differential scanning calorimetry, for the thermal transition that corresponds to the solid-to-liquid phase change.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable with other components of the composition. Such pharmaceutically acceptable materials typically have met the required standards of toxicological and manufacturing testing, and include those materials identified as suitable inactive ingredients by the U.S. Food and Drug Administration.

The term "therapeutically effective amount" means an amount sufficient to effect treatment when administered to a patient in need thereof, i.e., the amount of drug needed to obtain the desired therapeutic effect. For example, a therapeutically effective amount for treating hypertension is an amount of compound needed to, for example, reduce, suppress, eliminate or prevent the symptoms of hypertension, or to treat the underlying cause of hypertension. In one embodiment, a therapeutically effective amount is that amount needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising an $AT_1$ receptor, an "effective amount" may be the amount needed to antagonize the receptor.

The term "treating" or "treatment" as used herein means the treating or treatment of a disease or medical condition (such as hypertension) in a patient, such as a mammal (particularly a human) that includes: (a) preventing the disease or medical condition from occurring, that is, prophylactic treatment of a patient; (b) ameliorating the disease or medical condition such as by eliminating or causing regression of the disease or medical condition in a patient; (c) suppressing the disease or medical condition such as by slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "patient" is intended to include those mammals, such as humans, that are in need of treatment or disease prevention or that are presently being treated for disease prevention or treatment of a specific disease or medical condition. The term "patient" also includes test subjects in which compounds of the invention are being evaluated or test subjects being used in a assay, for example an animal model.

General Synthetic Procedures

The crystalline compound of the invention can be synthesized from readily available starting materials as described below and in the Examples. There are several methods that can be used to produce the crystalline compound of the invention. It is noted, however, that the crystalline content as well as the habit of the crystals (size and shape) may vary, based partly upon the method of preparation, as well as on the solvent composition. The crystals have been observed as having a plate and needle morphology.

It will be appreciated that while specific process conditions (i.e. crystallization temperatures, times, mole ratios of reactants, solvents, pressures, etc.) are given, other process conditions can also be used unless otherwise stated. In some instances, reactions or crystallizations were conducted at room temperature and no actual temperature measurement was taken. It is understood that room temperature can be taken to mean a temperature within the range commonly associated with the ambient temperature in a laboratory environment, and will typically be in the range of about 25° C. to about 50° C. In other instances, reactions or crystallizations were conducted at room temperature and the temperature was actually measured and recorded.

Generally, the crystallizations are conducted in a suitable inert diluent or solvent system, examples of which include, but are not limited to, methanol, ethanol, isopropanol, isobutanol, ethyl acetate, acetonitrile, dichloromethane, methyl t-butyl ether, and the like, and mixtures thereof, optionally containing water. Upon completion of any of the foregoing crystallizations, the crystalline compound can be isolated from the reaction mixture by any conventional means such as precipitation, concentration, centrifugation and the like.

The 4'-{2-ethoxy-4-ethyl-5-[((S)-2-mercapto-4-methylpentanoylamino)methyl]-imidazol-1-ylmethyl}-3'-fluorobiphenyl-2-carboxylic acid employed in the invention can be readily prepared from commercially available starting materials and reagents using the procedures described in the Examples, or using the procedures described in the commonly-assigned U.S. applications described in the Background section of this application. The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

In general, the crystalline form of the compound of formula I can be prepared by treating 4'-{2-ethoxy-4-ethyl-5-[((S)-2-mercapto-4-methylpentanoylamino)methyl]-imidazol-1-ylmethyl}-3'-fluorobiphenyl-2-carboxylic acid with an inert diluent to complete dissolution. Suitable inert diluents include by way of illustration and not limitation, acetone, acetonitrile, ethyl acetate, methyl ethyl ketone, methanol, ethanol, isopropanol, water, and so forth. Other suitable inert diluents include by way of illustration and not limitation, combinations of inert diluents such as acetone with water, acetonitrile with water, and methanol and water. In one particular embodiment, the inert diluent is acetone, acetonitrile or a combination of acetone with water. Generally, dissolution is conducted at a temperature ranging from about 20° C. to about 50° C., in one embodiment at a temperature ranging from about 30-45° C., and in another embodiment at a temperature of about 15-25° C. The solution is then cooled to form the crystalline compound of the invention. In one particular embodiment, the solution is cooled to about 20-30° C. such as 25° C., and in and in another embodiment to about 0-8° C. such as 4° C. After a suitable amount of time, crystals will be observed. In one embodiment, crystals are observed after a period of about 20-24 hours, and in another embodiment, observed after a period of about 4 hours. Once crystals are observed, the volume of the mother liquor can be reduced and the crystals isolated and dried.

In one embodiment, the crystalline compound of the invention is prepared by treating 4'-{2-ethoxy-4-ethyl-5-[((S)-2-mercapto-4-methylpentanoylamino)methyl]-imidazol-1-ylmethyl}-3'-fluorobiphenyl-2-carboxylic acid with acetone to complete dissolution and cooling to effect crystallization. The resulting solids can then be isolated and dried to yield the crystalline compound of the invention. Typically, this process can be conducted at any of the aforementioned temperature ranges. In one embodiment, the dissolution step is conducted at about 30-45° C., for example, at about 35-40° C., and the cooling step is conducted at about 0-8° C., for example, at about 4° C.

In another embodiment, the crystalline compound of the invention is prepared by treating 4'-{2-ethoxy-4-ethyl-5-[((S)-2-mercapto-4-methylpentanoylamino)methyl]-imidazol-1-ylmethyl}-3'-fluorobiphenyl-2-carboxylic acid with acetonitrile to complete dissolution and cooling to effect crystallization. The resulting solids can then be isolated and dried to yield the crystalline compound of the invention. Typically, this process can be conducted at any of the aforementioned temperature ranges. In one embodiment, the dissolution step is conducted at about 30-45° C., for example, at about 35° C., and the cooling step is conducted at about 0-8° C., for example, at about 4° C.

In another embodiment, the crystalline compound of the invention is prepared using a thiol-protected form of 4'-{2-ethoxy-4-ethyl-5-[((S)-2-mercapto-4-methylpentanoylamino)methyl]imidazol-1-ylmethyl}-3'-fluorobiphenyl-2-carboxylic acid. This method involves deprotecting 4'-{5-[((S)-2-acetylsulfanyl-4-methylpentanoylamino)methyl]-2-ethoxy-4-ethylimidazol-1-ylmethyl}-3'-fluorobiphenyl-2-carboxylic acid in methanol, and adding water to complete dissolution and cooling to effect crystallization. Standard deprotection techniques and reagents such as NaOH, sodium methoxide, primary alkylamines, and hydrazine, may be used to remove the thiol protecting group. The deprotection step may include a reducing agent such as 1,4-dithiothreitol. The resulting solids can then be isolated and dried to yield the crystalline compound of the invention. Typically, this process can be conducted at any of the aforementioned temperature ranges. In one embodiment, the deprotection step is conducted at about −5° C. to 5° C., for example at about 0° C., the dissolution step is conducted at about 15-25° C., for example, at about 20° C., and the cooling step is conducted at about 0-8° C., for example, at about 4° C.

Crystalline Properties

Among other advantages, it has been discovered that forming a crystalline form of the compound of formula I, is useful for purifying the compound itself. For example, the crystalline compound of the invention has a purity of 98.5%.

As is well known in the field of powder x-ray diffraction, relative peak heights of PXRD spectra are dependent on a number of factors relating to sample preparation and instrument geometry, while peak positions are relatively insensitive to experimental details. A PXRD pattern was obtained as set forth in Example 3. Thus, in one embodiment, the crystalline compound of the invention is characterized by a PXRD pattern having certain peak positions.

The crystalline form of the compound of formula I is characterized by a PXRD pattern in which the peak positions are substantially in accordance with those shown in FIG. 1. Those peaks are listed below, in order of descending relative intensity.

| I %  | 2-Theta |
|------|---------|
| 100  | 18.121  |
| 76   | 6.658   |
| 64   | 9.801   |
| 62   | 22.621  |
| 52   | 19.324  |
| 51   | 24.561  |
| 44   | 12.682  |
| 40   | 15.019  |
| 37   | 25.296  |
| 30   | 27.318  |
| 27   | 13.543  |
| 27   | 21.199  |
| 19   | 25.958  |

Thus, in one embodiment, the crystalline compound of the invention is characterized by a powder x-ray diffraction (PXRD) pattern comprising diffraction peaks at 2θ values of 6.66±0.20, 9.8±0.20, and 18.12±0.20; and further characterized by having one or more additional diffraction peaks at 2θ values selected from 12.68±0.20, 13.54±0.20, 15.02±0.20, 19.32±0.20, 21.20±0.20, 22.62±0.20, 24.56±0.20, 25.30±0.20, 25.96±0.20, and 27.32±0.20.

Figure 2:
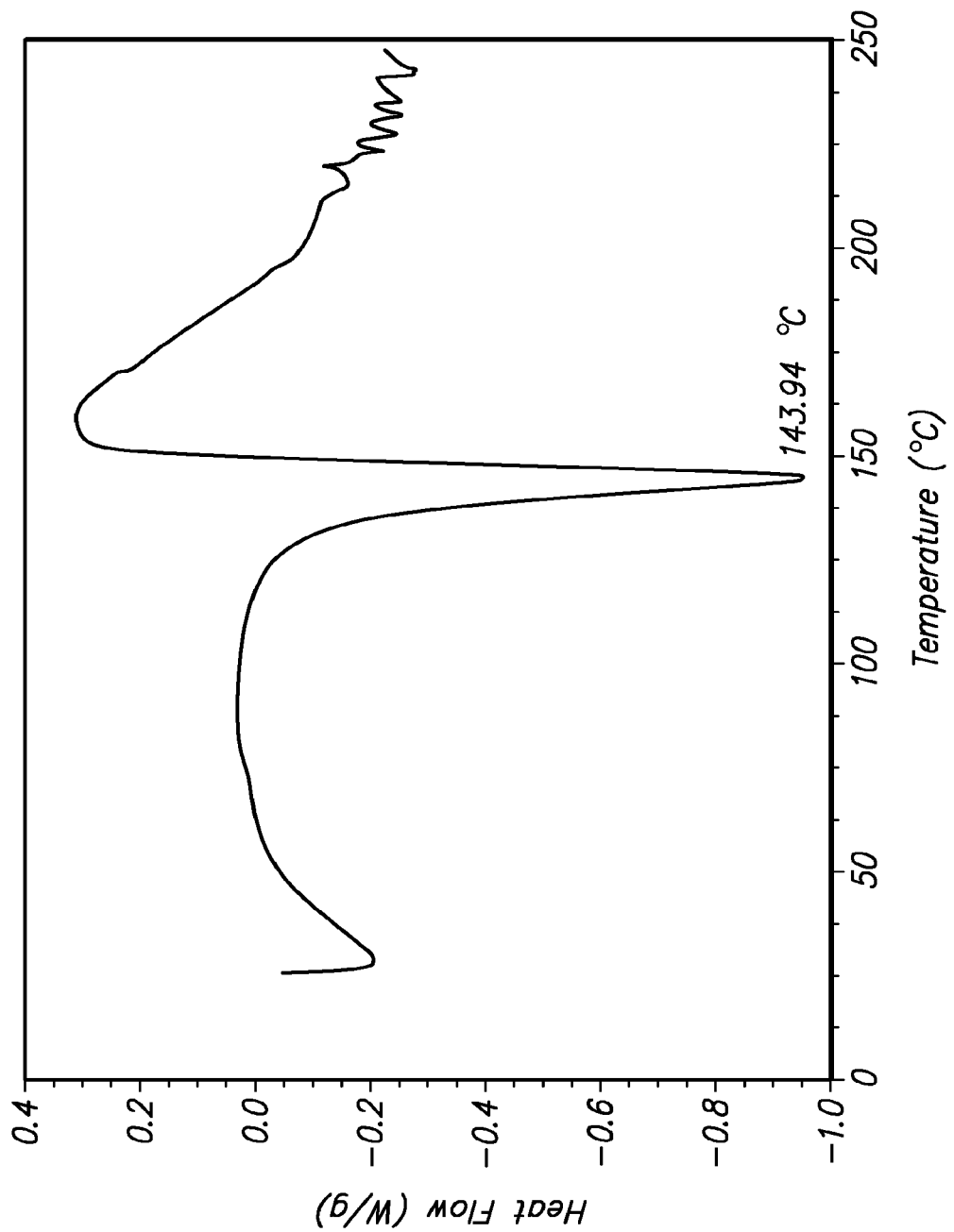
FIG. 2 shows a differential scanning calorimetry (DSC) thermograph for the crystalline form of the compound of formula I.

A differential scanning calorimetry (DSC) trace was obtained as set forth in Example 4. Thus, in one embodiment, the crystalline compound of the invention is characterized by its DSC thermograph. In one embodiment, the crystalline compound of the invention is characterized by a DSC thermograph which shows a melting point of about 144° C., with no significant thermal decomposition below about 150° C., as seen in FIG. 2.

Figure 3:
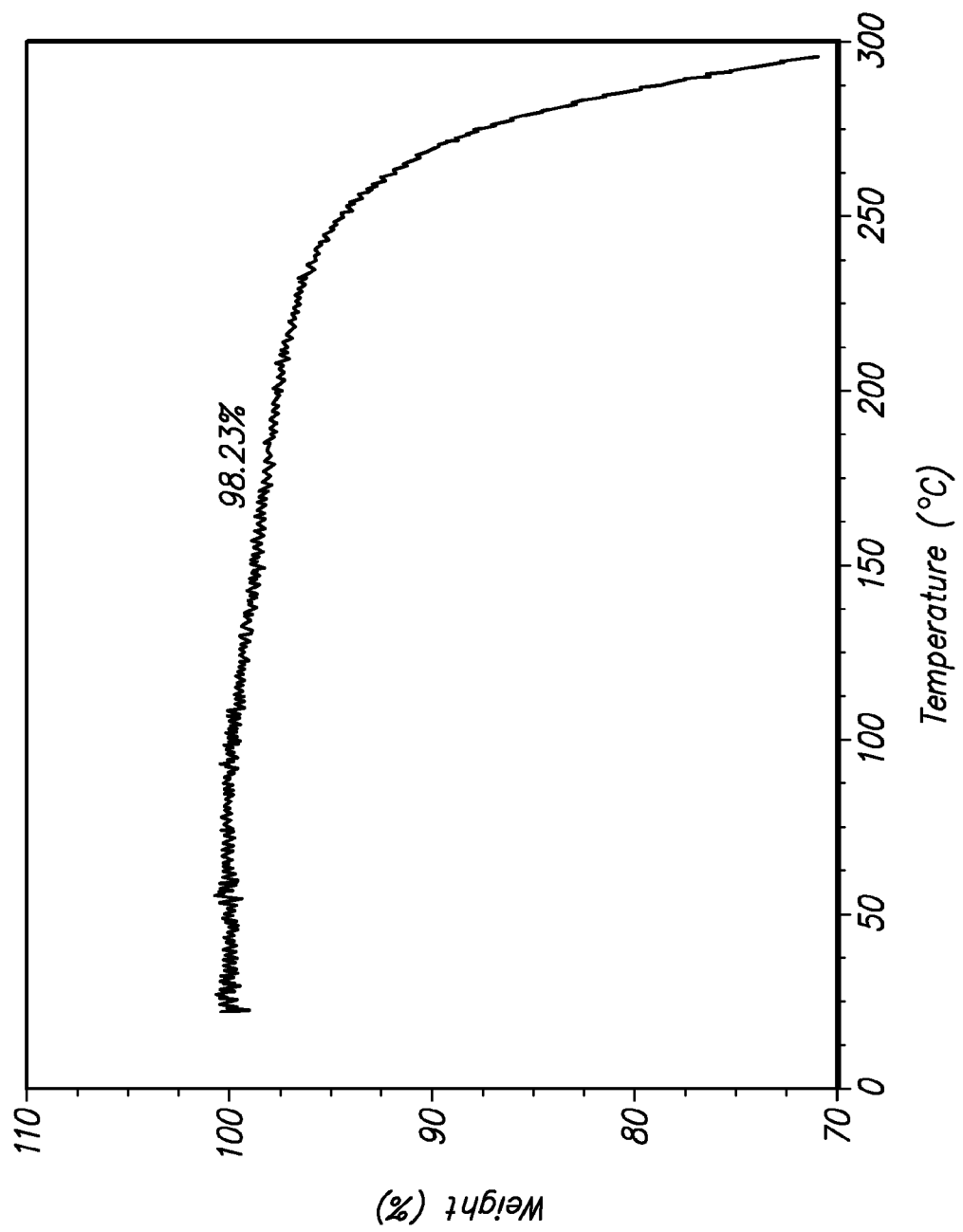
FIG. 3 shows a thermal gravimetric analysis (TGA) trace for the crystalline form of the compound of formula I.

Thermogravimetric analysis (TGA) was performed on the crystalline compound of the invention as described in Example 4. Thus, in one embodiment, the crystalline compound of the invention is characterized by its TGA trace. In one embodiment, the crystalline compound of the invention is characterized by a TGA trace which shows a loss of solvents and/or water (1.8%) at temperatures below about 200° C. (which is significantly higher than the melting point), as seen in FIG. 3.

Figure 4:
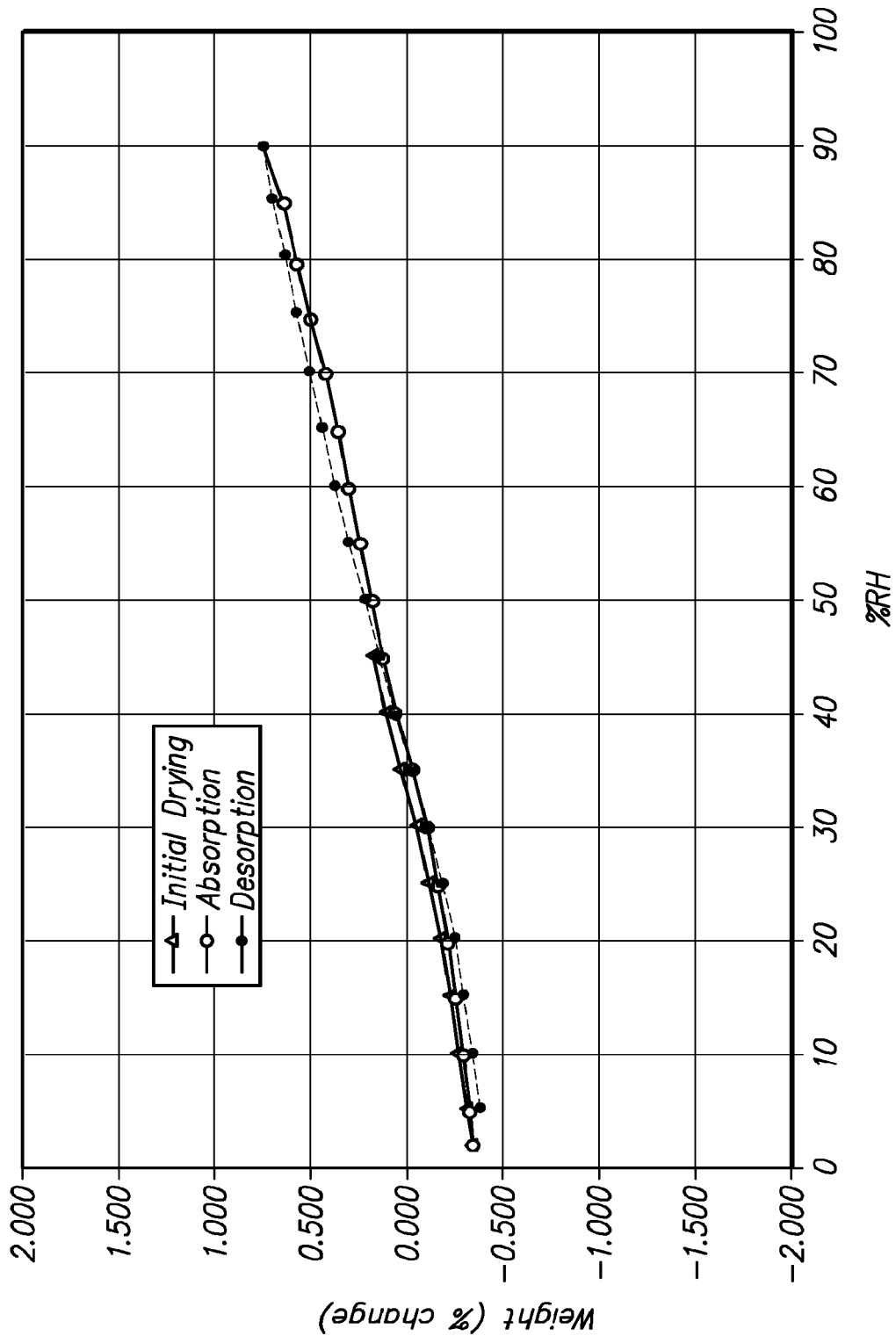
FIG. 4 shows a dynamic moisture sorption (DMS) profile for the crystalline form of the compound of formula I.

The crystalline compound of the invention has been demonstrated to have a reversible sorption/desorption profile with acceptable levels of hygroscopicity. For example, the crystalline form of the compound of formula I has no or minimal hygroscopicity propensity, and has exhibited less than about 1% weight gain when exposed to up to 75% relative humidity, as seen in FIG. 4.

Figure 5:
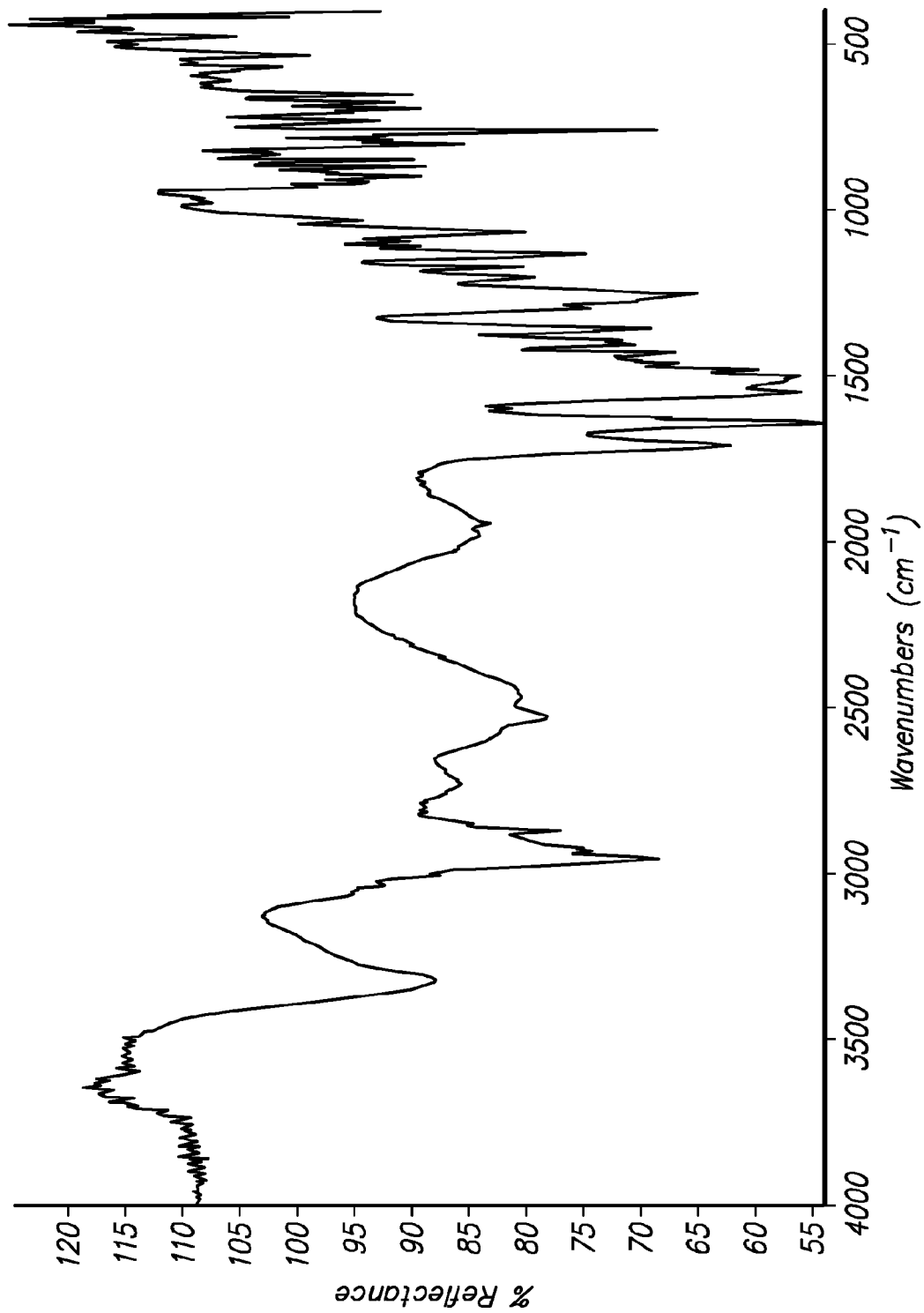
FIG. 5 shows an infrared (TR) absorption spectra for the crystalline form of the compound of formula I.
Figure 6:
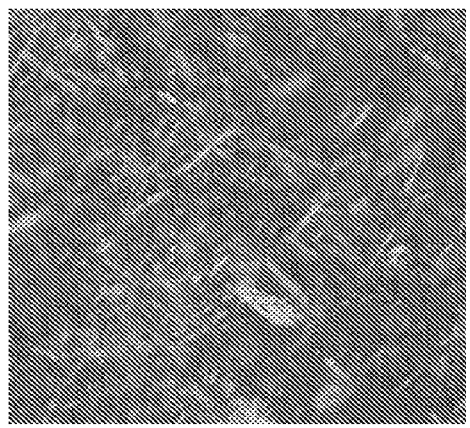
FIG. 6 is a micrographic image of the crystalline form of the compound of formula I.

The infrared (IR) absorption spectrum of the crystalline compound of the invention was obtained as described in Example 10. Thus, in one embodiment, the crystalline compound of the invention is characterized by an IR absorption spectrum having significant absorption bands at 3324±1, 2958±1, 2872±1, 2527±1, 1709±1, 1643±1, 1551±1, 1500±1, 1357±1, 1254±1, 1133±1, 1062±1, 869±1, 799±1, 759±1, and 695±1 cm$^{-1}$, as seen in FIG. 5.

Additionally, the crystalline compound of the invention has been found to be stable upon exposure to elevated temperatures. For example, after storage for 28 days at 40° C., analysis of the crystalline freebase by high performance liquid chromatography (HPLC) showed minimal chemical degradation.

These properties of the crystalline compound of the invention are further illustrated in the Examples below.

Utility

The compound of formula I possesses angiotensin II type 1 ($AT_1$) receptor antagonist activity and neprilysin (NEP) inhibition activity, i.e., the compound is able to inhibit enzyme-substrate activity. One measure of the affinity of a compound for the $AT_1$ receptor is the inhibitory constant ($K_i$) for binding to the $AT_1$ receptor. The $pK_i$ value is the negative logarithm to base 10 of the $K_i$. One measure of the ability of a compound to inhibit NEP activity is the inhibitory concentration ($IC_{50}$), which is the concentration of compound that results in half-maximal inhibition of substrate conversion by the NEP enzyme. The $pIC_{50}$ value is the negative logarithm to base 10 of the $IC_{50}$. The compound of formula I exhibits a $pK_i$ at the $AT_1$ receptor greater than or equal to about 7.0, and exhibit a $pIC_{50}$ for NEP greater than or equal to about 7.0.

Exemplary assays to determine properties of the compound of formula I as well as of the crystalline compound of the invention, such as the $AT_1$ receptor binding and/or NEP inhibiting activity, are described in the Examples and include by way of illustration and not limitation, assays that measure $AT_1$ and $AT_2$ binding (described in Assay 1), and NEP inhibition (described in Assay 2). Useful secondary assays include assays to measure angiotensin converting enzyme (ACE) inhibition (also described in Assay 2) and aminopeptidase P (APP) inhibition (described in Sulpizio et al. (2005) JPET 315:1306-1313). A pharmacodynamic assay to assess the in vivo inhibitory potencies for ACE, $AT_1$, and NEP in anesthetized rats is described in U.S. Publication Nos. 2008/0269305 and 2009/0023228, both to Allegretti et al. (see also Seymour et al. Hypertension 7(Suppl I):1-35-I-42, 1985 and Wigle et al. Can. J. Physiol. Pharmacol. 70:1525-1528, 1992), where $AT_1$ inhibition is measured as the percent inhibition of the angiotensin II pressor response, ACE inhibition is measured as the percent inhibition of the angiotensin I pressor response, and NEP inhibition is measured as increased urinary cyclic guanosine 3',5'-monophosphate (cGMP) output. Useful in vivo assays include the conscious spontaneously hypertensive rat (SHR) model, a renin dependent hypertension model that is useful for measuring $AT_1$ receptor blocking (described in U.S. Publication Nos. 2008/0269305 and 2009/0023228, both to Allegretti et al.; see also Intengan et al. (1999) Circulation 100(22):2267-2275 and Badyal et al. (2003) Indian Journal of Pharmacology 35:349-362), and the conscious desoxycorticosterone acetate-salt (DOCA-salt) rat model, a volume dependent hypertension model that is useful for measuring NEP activity (described in U.S. Publication Nos. 2008/0269305 and 2009/0023228, both to Allegretti et al.; see also Trapani et al. (1989) J. Cardiovasc. Pharmacol. 14:419-424, Intengan et al. (1999) Hypertension 34(4):907-913, and Badyal et al. (2003) supra). Both the SHR and DOCA-salt models are useful for evaluating the ability of a test compound to reduce blood pressure. The DOCA-salt model is also useful to measure a test compound's ability to prevent or delay a rise in blood pressure.

The compound of formula I as well as of the crystalline compound of the invention are expected to antagonize the $AT_1$ receptor and inhibit the NEP enzyme in any of the assays listed above, or assays of a similar nature. Thus, the aforementioned assays are useful in determining the therapeutic utility of the crystalline compound of the invention, for example, its utility as an antihypertensive agent. Other properties and utilities of the crystalline compound can be demonstrated using other in vitro and in vivo assays well-known to those skilled in the art.

Therefore, the crystalline form of the compound of formula I is expected to find utility in the treatment and/or prevention of medical conditions responsive to $AT_1$ receptor antagonism and NEP inhibition. For example, by antagonizing the $AT_1$ receptor and thus interfering with the action of angiotensin II on its receptors, the crystalline compound of the invention is expected to find utility in preventing the increase in blood pressure produced by angiotensin II, a potent vasopressor. In addition, by inhibiting NEP, the crystalline compound is also expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. For example, by potentiating the effects of the natriuretic peptides, the crystalline compound is expected to be useful to treat glaucoma. This crystalline compound is also expected to have other physiological actions, for example, on the renal, central nervous, reproductive and gastrointestinal systems.

The crystalline compound of the invention is expected to find utility in treating and/or preventing medical conditions such as cardiovascular and renal diseases. Cardiovascular diseases of particular interest include heart failure such as congestive heart failure, acute heart failure, chronic heart failure, and acute and chronic decompensated heart failure. Renal diseases of particular interest include diabetic nephropathy and chronic kidney disease. One embodiment of the invention is directed to a method for treating hypertension, comprising administering to a patient a therapeutically effective amount of the crystalline compound of the invention. Typically, the therapeutically effective amount is the amount that is sufficient to lower the patient's blood pressure. In one embodiment, the crystalline compound is administered as an oral dosage form.

Another embodiment of the invention is directed to a method for treating heart failure, comprising administering to a patient a therapeutically effective amount of the crystalline compound of the invention. Typically, the therapeutically effective amount is the amount that is sufficient to lower blood pressure and/or improve renal functions. In one embodiment, the crystalline compound is administered as an intravenous dosage form. When used to treat heart failure, the crystalline compound may be administered in combination with other therapeutic agents such as diuretics, natriuretic peptides, and adenosine receptor antagonists.

The crystalline compound of the invention is also expected to be useful in preventative therapy, for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

In addition, as a NEP inhibitor, the crystalline compound of the invention is expected to inhibit enkephalinase, which will inhibit the degradation of endogenous enkephalins and thus such compounds may also find utility as analgesics. Due to its NEP inhibition properties, the crystalline compound is also expected to be useful as antitussive agents and antidiarrheal agents (for example, for the treatment of watery diarrhea), as well as find utility in the treatment of menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, the crystalline compound is expected to be useful in treating female sexual dysfunction, which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, the crystalline compound may be combined with one or more of the following secondary agents: PDE5 inhibitors, dopamine agonists, estrogen receptor agonists and/or antagonists, androgens, and estrogens.

The amount of the crystalline compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of the crystalline compound will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Since the crystalline compound of the invention possesses $AT_1$ receptor antagonist activity and NEP enzyme inhibition activity, its is also useful as a research tool for investigating or studying biological systems or samples having $AT_1$ receptors or a NEP enzyme, for example to study diseases where the $AT_1$ receptor or NEP enzyme plays a role. Any suitable biological system or sample having $AT_1$ receptors and/or a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention an $AT_1$ receptor in a mammal is antagonized by administering an $AT_1$-antagonizing amount of the crystalline compound. In another particular embodiment, NEP enzyme activity in a mammal is inhibited by administering a NEP-inhibiting amount of the crystalline compound. The crystalline compound can also be used as a research tool by conducting biological assays using such compound.

When used as a research tool, a biological system or sample comprising an $AT_1$ receptor and/or a NEP enzyme is typically contacted with an $AT_1$ receptor-antagonizing or NEP enzyme-inhibiting amount of the crystalline compound. After the biological system or sample is exposed to the crystalline compound, the effects of antagonizing the $AT_1$ receptor and/or inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the compound to a mammal, for example by i.p., i.v. or s.c. administration, and so forth. This determining step can involve measuring a response (a quantitative analysis) or can involve making an observation (a qualitative analysis). Measuring a response involves, for example, determining the effects of the crystalline compound on the biological system or sample using conventional procedures and equipment, such as radioligand binding assays and measuring ligand-mediated changes in functional assays. The assay results can be used to determine the activity level as well as the amount of compound necessary to achieve the desired result, that is, an $AT_1$ receptor-antagonizing and/or a NEP enzyme-inhibiting amount. Typically, the determining step will involve determining the $AT_1$ receptor ligand-mediated effects and/or determining the effects of inhibiting the NEP enzyme.

Additionally, the crystalline compound of the invention can be used as a research tool for evaluating other chemical compounds, and thus are also useful in screening assays to discover, for example, new compounds having $AT_1$ receptor-antagonizing activity and/or NEP-inhibiting activity. In this manner, the crystalline compound is used as a standard in an assay to allow comparison of the results obtained with a test compound and with the crystalline compound to identify those test compounds that have about equal or superior activity, if any. For example, $K_i$ data (as determined, for example, by a binding assay) for a test compound or a group of test compounds is compared to the $K_i$ data for the crystalline compound of the invention to identify those test compounds that have the desired properties, for example, test compounds having a $K_i$ value about equal or superior to a compound of the invention, if any. This aspect of the invention includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include an $AT_1$ receptor binding assay and a NEP enzyme inhibition assay.

Pharmaceutical Compositions and Formulations

The crystalline compound of formula I is typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, the compounds of the invention may be administered, for example orally, in multiple doses per day (for example, two, three, or four times daily), in a single daily dose or a single weekly dose. It will be understood by those skilled in the art that, once the crystalline compound of the invention has been formulated, it may no longer be in crystalline form, i.e., the crystalline compound may be dissolved in a suitable carrier.

Accordingly, in one embodiment, the invention relates to a pharmaceutical composition comprising a pharmaceutically acceptable carrier and a crystalline form of 4'-{2-ethoxy-4-ethyl-5-[((S)-2-mercapto-4-methylpentanoylamino)methyl]imidazol-1-ylmethyl}-3'-fluorobiphenyl-2-carboxylic acid. Such pharmaceutical compositions may also contain other therapeutic and/or formulating agents if desired. When discussing compositions, the "crystalline compound of the invention" may also be referred to herein as the "active agent" to distinguish it from other components of the formulation, such as the carrier.

The pharmaceutical compositions of the invention typically contain a therapeutically effective amount of the crystalline compound of the invention. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

Since the crystalline compound of the invention contains a thiol group, additional consideration may be given to minimize or eliminate oxidation of the thiol to form a disulfide. In solid formulations, this may be accomplished by reducing the drying time, decreasing the moisture content of the formulation, and including materials such as ascorbic acid, sodium ascorbate, sodium sulfite and sodium bisulfate, as well as materials such as a mixture of lactose and microcrystalline cellulose. In liquid formulations, stability of the thiol may be improved by the addition of amino acids, antioxidants, or a combination of disodium edetate and ascorbic acid.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in microencapsulated form, optionally with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's air-stream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

The crystalline compound of the invention can also be administered parenterally (for example, by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages, or dimerization of the thiol that is present in the compound. These formulations may be rendered sterile by use of a sterile injectable medium, a sterilizing agent, filtration, irradiation, or heat. In one particular embodiment, the parenteral formulation comprises an aqueous cyclodextrin solution as the pharmaceutically acceptable carrier. Suitable cyclodextrins include cyclic molecules containing six or more α-D-glucopyranose units linked at the 1,4 positions by a linkages as in amylase, β-cyclodextrin or cycloheptaamylose. Exemplary cyclodextrins include cyclodextrin derivatives such as hydroxypropyl and sulfobutyl ether cyclodextrins such as hydroxypropyl-β-cyclodextrin and sulfobutyl ether β-cyclodextrin. Exemplary buffers for such formulations include carboxylic acid-based buffers such as citrate, lactate and maleate buffer solutions.

The crystalline compound of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, the crystalline compound of the invention may be administered in combination with one or more other therapeutic agents. Thus, in one embodiment, pharmaceutical compositions of the invention contain other drugs that are co-administered with the crystalline compound of the invention. For example, the composition may further comprise one or more therapeutic agents (also referred to as "secondary agents(s)") selected from the group of diuretics, $\beta_1$ adrenergic receptor blockers, calcium channel blockers, angiotensin-converting enzyme inhibitors, $AT_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, and combinations thereof. Such therapeutic agents are well known in the art, and examples are described below. By combining the crystalline compound of the invention with a secondary agent, triple therapy can be achieved; $AT_1$ receptor antagonist activity, NEP inhibition activity, and activity associated with the secondary agent (for example, $\beta_1$ adrenergic receptor blocker) can be achieved using only two active components. Since compositions containing two active components are typically easier to formulate than compositions containing three active components, such two-component compositions provide a significant advantage over compositions containing three active components. Accordingly, in yet another embodiment of the invention, a pharmaceutical composition comprises a crystalline compound of the invention, a second active agent, and a pharmaceutically acceptable carrier. Third, fourth etc. active agents may also be included in the composition. In combination therapy, the amount of crystalline compound of the invention that is administered, as well as the amount of secondary agents, may be less than the amount typically administered in monotherapy.

The crystalline compound of the invention may be physically mixed with the second active agent to form a composition containing both agents, or each agent may be present in separate and distinct compositions which are administered to the patient simultaneously or at separate times. For example, the crystalline compound can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the crystalline compound, ranging anywhere from concurrent with administration of the crystalline compound to about 24 hours post-dose. This is also referred to as sequential administration. Thus, the crystalline compound of the invention can be orally administered simultaneously or sequentially with another active agent using two tablets, with one tablet for each active agent, where sequential may mean being administered immediately after administration of the crystalline compound or at some predetermined time later (for example, one hour later or three hours later). Alternatively, the combination may be administered by different routes of administration, that is, one orally and the other by inhalation.

In one embodiment of the invention, a the kit comprises a first dosage form comprising the crystalline compound of the invention and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with the crystalline compound of the invention. Suitable doses for these secondary agents administered in combination with the crystalline compound of the invention are in the range of about 0.05 µg/day to about 100 mg/day. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed below are intended to include all such forms, and are commercially available or can be prepared using conventional procedures and reagents.

In one embodiment, the crystalline compound of the invention is administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosernide, bumetanide, butazolamide, chloraminophenamide, clofenamide, clopamide, clorexolone, disulfamide, ethoxolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and Na+ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

The crystalline compound of the invention may also be administered in combination with a $\beta_1$ adrenergic receptor blocker. Representative $\beta_1$ adrenergic receptor blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $\beta_1$ adrenergic receptor blocker is selected from atenolol, bisoprolol, metoprolol, propranolol, sotalol, and combinations thereof.

In one embodiment, the crystalline compound of the invention is administered in combination with a calcium channel blocker. Representative calcium channel blockers include, but are not limited to, amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexiline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof.

The crystalline compound of the invention can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltopril, pentopril, perindopril, quinapril, quinaprilat, ramipril, ramiprilat, saralasin acetate, spirapril, temocapril, trandolapril, zofenopril, and combinations thereof. In a particular embodiment, the ACE inhibitor is selected from: benazepril, enalapril, lisinopril, ramipril, and combinations thereof.

In one embodiment, the crystalline compound of the invention is administered in combination with an $AT_1$ receptor antagonist, also known as angiotensin II type 1 receptor blockers (ARBs). Representative ARBs include, but are not limited to, abitesartan, benzyllosartan, candesartan, candesartan cilexetil, elisartan, embusartan, enoltasosartan, eprosartan, fonsartan, forasartan, glycyllosartan, irbesartan, isoteoline, losartan, medoximil, milfasartan, olmesartan, opomisartan, pratosartan, ripisartan, saprisartan, saralasin, sarmesin, tasosartan, telmisartan, valsartan, zolasartan, and combinations thereof. In a particular embodiment, the ARB is selected from candesartan, eprosartan, irbesartan, losartan, olmesartan, irbesartan, saprisartan, tasosartan, telmisartan, and combinations thereof. Exemplary salts include eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

In another embodiment, the crystalline compound of the invention is administered in combination with a neprilysin (NEP) inhibitor. Representative NEP inhibitors include, but are not limited to: candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9 (R)-(acetylthiomethyl)-10-oxo-1-azacyclodecan-2(S)-ylcarbonyl]-4(R)-hydroxy-L-proline benzyl ester); 3-(1-carbamoylcyclohexyl)propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl)propionamide); SCH-32615 ((S)-N—[N-(1-carboxy-2-phenylethyl)-L-phenylalanyl]-β-alanine) and its prodrug SCH-34826 ((S)-N—[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-

(acetylsulfanylmethyl)-3-(2-methylphenyl)propionyl]-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-β-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino] cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl] cyclopentyl}propionic acid); 5-biphenyl-4-yl-4-(3-carboxypropionylamino)-2-methylpentanoic acid and 5-biphenyl-4-yl-4-(3-carboxypropionylamino)-2-methyl-pentanoic acid ethyl ester (WO 2007/056546); daglutril [(3S,2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis AG); and combinations thereof. In a particular embodiment, the NEP inhibitor is selected from candoxatril, candoxatrilat, CGS-24128, phosphoramidon, SCH-32615, SCH-34826, SQ-28603, thiorphan, and combinations thereof. The NEP inhibitor will be administered in an amount sufficient to provide from about 20-800 mg per day, with typical daily dosages ranging from 50-700 mg per day, more commonly 100-600 or 100-300 mg per day.

In yet another embodiment, the crystalline compound of the invention is administered in combination with a non-steroidal anti-inflammatory agent (NSAID). Representative NSAIDs include, but are not limited to: acemetacin, acetyl salicylic acid, alclofenac, alminoprofen, amfenac, amiprilose, amoxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In yet another embodiment, the crystalline compound of the invention is administered in combination with an anti-lipid agent. Representative anti-lipid agents include, but are not limited to, statins such as atorvastatin, fluvastatin, lovastatin, pravastatin, rosuvastatin and simvastatin; cholesteryl ester transfer proteins (CETPs); and combinations thereof.

In yet another embodiment, the crystalline compound of the invention is administered in combination with an anti-diabetic agent. Representative anti-diabetic agents include, but are not limited to: injectable drugs such as insulin and insulin derivatives; orally effective drugs including biguanides such as metformin, glucagon antagonists, α-glucosidase inhibitors such as acarbose and miglitol, meglitinides such as repaglinide, oxadiazolidinediones, sulfonylureas such as chlorpropamide, glimepiride, glipizide, glyburide, and tolazamide, thiazolidinediones such as pioglitazone and rosiglitazone; and combinations thereof.

In one embodiment, the crystalline compound of the invention is administered in combination with an anti-thrombotic agent. Representative anti-thrombotic agents include, but are not limited to, aspirin, anti-platelet agents, heparin, and combinations thereof. Compounds of the invention may also be administered in combination with a renin inhibitor, examples of which include, but are not limited to, aliskiren, enalkiren, remikiren, and combinations thereof. In another embodiment, a compound of the invention is administered in combination with an endothelin receptor antagonist, representative examples of which include, but are not limited to, bosentan, darusentan, tezosentan, and combinations thereof. Compounds of the invention may also be administered in combination with an endothelin converting enzyme inhibitor, examples of which include, but are not limited to, phosphoramidon, CGS 26303, and combinations thereof. In yet another embodiment, a compound of the invention is administered in combination with an aldosterone antagonist, representative examples of which include, but are not limited to, eplerenone, spironolactone, and combinations thereof.

Combined therapeutic agents may also be helpful in further combination therapy with compounds of the invention. For example, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with the compounds of the invention. Dual-acting agents may also be helpful in combination therapy with the crystalline compound of the invention. For example, angiotensin-converting enzyme/neprilysin (ACE/NEP) inhibitors such as: AVE-0848 ((4S,7S,12bR)-7-[3-methyl-2(S)-sulfanylbutyramido]-6-oxo-1,2,3,4,6,7,8,12b-octahydropyrido[2,1-a][2]benzazepine-4-carboxylic acid); AVE-7688 (ilepatril) and its parent compound; BMS-182657 (2-[2-oxo-3(S)-[3-phenyl-2(S)-sulfanylpropionamido]-2,3,4,5-tetrahydro-1H-1-benzazepin-1-yl]acetic acid); CGS-26303 ([N-[2-(biphenyl-4-yl)-1(S)-(1H-tetrazol-5-yl) ethyl]amino]methylphosphonic acid); CGS-35601 (N-[1-[4-methyl-2(S)-sulfanylpentanamido]cyclopentylcarbonyl]-L-tryptophan); fasidotril; fasidotrilate; enalaprilat; ER-32935 ((3R,6S,9aR)-6-[3(S)-methyl-2(S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8,12b-octahydropyrido[2,1-a][2]benzazepine-4-carboxylic acid); MDL-101287 ([4S-[4α,7α(R*),12bβ]]-7-[2-(carboxymethyl)-3-phenylpropionamido]-6-oxo-1,2,3,4,6,7,8,12b-octahydropyrido[2,1-a][2]benzazepine-4-carboxylic acid); omapatrilat; RB-105 (N-[2(S)-(mercaptomethyl)-3 (R)-phenylbutyl]-L-alanine); sampatrilat; SA-898 ((2R,4R)-N-[2-(2-hydroxyphenyl)-3-(3-mercaptopropionyl)thiazolidin-4-ylcarbonyl]-L-phenylalanine); Sch-50690 (N-[1(S)-carboxy-2-[N2-(methanesulfonyl)-L-lysylamino]ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine. Exemplary vasopressin receptor antagonists include tolvaptan.

The following formulations illustrate representative pharmaceutical compositions of the invention.

Exemplary Hard Gelatin Capsules For Oral Administration

The crystalline compound of the invention (50 g), spray-dried lactose (440 g) and magnesium stearate (10 g) are thoroughly blended. The resulting composition is then loaded into hard gelatin capsules (500 mg of composition per capsule). Alternately, the crystalline compound (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Exemplary Gelatin Capsule Formulation For Oral Administration

The crystalline compound of the invention (100 mg) is thoroughly blended with polyoxyethylene sorbitan monooleate (50 mg) and starch powder (250 mg). The mixture is then loaded into a gelatin capsule (400 mg of composition per capsule).

Alternately, the crystalline compound (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation For Oral Administration

The crystalline compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, the crystalline compound (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, the crystalline compound (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, the crystalline compound (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are the admixed with the gelatin formulation, granulated and the resulting mixture compressed to form tablets (100 mg of active per tablet).

Exemplary Suspension Formulation For Oral Administration

The following ingredients are mixed to form a suspension containing 100 mg of active agent per 10 mL of suspension:

| Ingredients | Amount |
|---|---|
| Crystalline compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum® K (magnesium aluminum silicate) | 1.0 g |
| Flavoring | 0.035 mL |
| Colorings | 0.5 mg |
| Distilled water | q.s. to 100 mL |

Exemplary Liquid Formulation For Oral Administration

A suitable liquid formulation is one with a carboxylic acid-based buffer such as citrate, lactate and maleate buffer solutions. For example, the crystalline compound of the invention (which may be pre-mixed with DMSO) is blended with a 100 mM ammonium citrate buffer and the pH adjusted to pH 5, or with is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Other suitable formulations include a 5% $NaHCO_3$ solution, with or without cyclodextrin.

Exemplary Injectable Formulation for Administration by Injection

The crystalline compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration by Inhalation

The crystalline compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, the micronized crystalline compound (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.

Alternately, the crystalline compound (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N sodium hydroxide. The solution is administered using a nebulizer device that provides about 10 μg to about 500 μg of the active agent per dose.

EXAMPLES

The following Preparations and Examples are provided to illustrate specific embodiments of this invention. These specific embodiments, however, are not intended to limit the scope of this invention in any way unless specifically indicated.

The following abbreviations have the following meanings unless otherwise indicated and any other abbreviations used herein and not defined have their standard generally accepted meaning:

| | |
|---|---|
| AcOH | acetic acid |
| $AT_1$ | angiotensin II type 1 (receptor) |
| $AT_2$ | angiotensin II type 2 (receptor) |
| BSA | bovine serum albumin |
| $Bu_4NBr$ | tetrabutylammonium bromide |
| DCC | 1,3-dicyclohexylcarbodiimide |
| DCM | dichloromethane or methylene chloride |
| DIPEA | N,N-diisopropylethylamine |
| DMAP | 4-dimethylaminopyridine |
| DMF | N,N-dimethylformamide |
| DMSO | dimethyl sulfoxide |
| Dnp | 2,4-dinitrophenyl |
| DOCA | deoxycorticosterone acetate |
| DTT | 1,4-dithiothreitol |
| EDC | N-(3-dimethylaminopropyl)-N'-ethylcarbodiimide |
| EDTA | ethylenediaminetetraacetic acid |
| EGTA | ethylene glycol bis(β-aminoethyl ether)-N,N,N'N'-tetraacetic acid |
| EtOAc | ethyl acetate |
| EtOH | ethanol |
| HATU | N,N,N',N'-tetramethyl-O-(7-azabenzotriazol-1-yl)uronium hexafluorophosphate |
| HCTU | (2-(6-chloro-1H-benzotriazole-1-y1)-1,1,3,3-tetramethylaminium hexafluorophosphate) |
| IPAc | isopropyl acetate |
| Mca | (7-methoxycoumarin-4-yl)acyl |
| MeCN | acetonitrile |
| MeOH | methanol |
| MTBE | methyl t-butyl ether |

-continued

| | |
|---|---|
| NaOMe | sodium methoxide |
| NBS | N-bromosuccinimide |
| NEP | neprilysin (EC 3.4.24.11) |
| PBS | phosphate buffered saline |
| SHR | spontaneously hypertensive rat |
| TFA | trifluoroacetic acid |
| THF | tetrahydrofuran |
| Tris | tris(hydroxymethyl)aminomethane |
| Tween-20 | polyethylene glycol sorbitan monolaurate |

Unless noted otherwise, all materials, such as reagents, starting materials and solvents, were purchased from commercial suppliers (such as Sigma-Aldrich, Fluka Riedel-de Haën, Strem Chemicals, Inc., and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Solvents used in analytical HPLC were as follows: solvent A was 98% water/2% MeCN/1.0 mL/L TFA; solvent B was 90% MeCN/10% water/1.0 mL/L TFA.

Reactions were worked up as described specifically in each preparation or example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Characterization of reaction products was routinely carried out by mass and $^1$H-NMR spectrometry. For NMR measurement, samples were dissolved in deuterated solvent ($CD_3OD$, $CDCl_3$, or DMSO-$d_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Preparation 1

5-Bromo-2-ethoxy-3H-imidazole-4-carbaldehyde 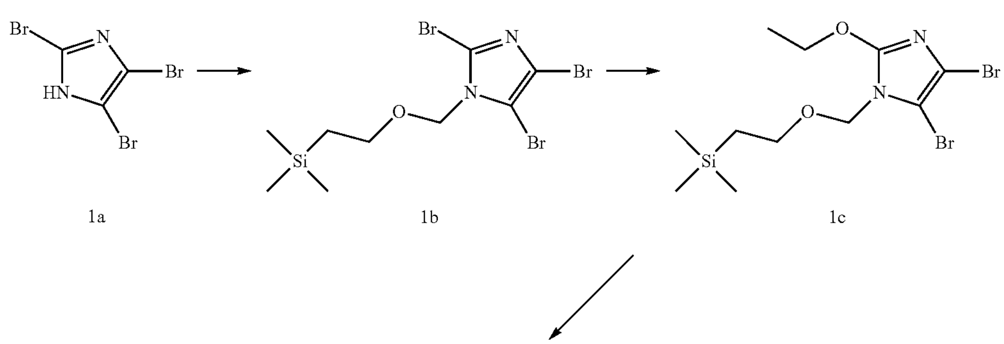 1a 1b 1c

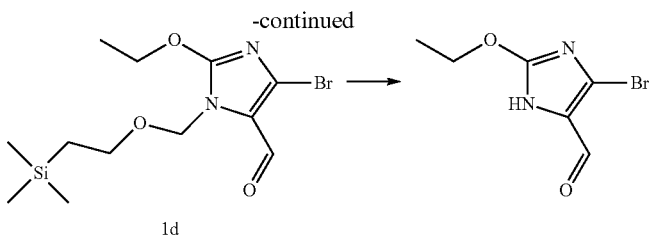

1d 2,4,5-Tribromo-1H-imidazole (1a) (98.7 g, 324 mmol, 1.0 eq) was dissolved into 1.20 L of DCM and cooled to 0° C. To this was added DIPEA (62 mL, 360 mmol, 1.1 eq) followed by the slow addition of [β-(trimethylsilyl)ethoxy]methyl chloride (60.2 mL, 340 mmol, 1.05 eq). The solution was slowly warmed to room temperature. After 2 hours the mixture was washed with 1M $H_3PO_4$/saturated aqueous NaCl (1:10; 2×600 mL). The organic layer was dried over $MgSO_4$, and evaporated to dryness, yielding intermediate (1b) as faint yellow liquid that solidified on standing (137 g).

Intermediate (1b) (130 g, 290 mmol, 1.0 eq) was dissolved into anhydrous EtOH (650 mL). To this was slowly added potassium t-butoxide (98.6 g, 879 mmol, 3.0 eq) and the mixture was heated to reflux for 16 hours. The mixture was then cooled to room temperature, filtered and concentrated. The resulting oil was dissolved in EtOAc (800 mL) and washed with saturated $NaHCO_3$ (400 mL). The layers were separated and the organic was washed with saturated aqueous NaCl, dried over $MgSO_4$, filtered and concentrated, yielding intermediate (1c) as a brown oil (115.3 g). MS m/z: [M+H$^+$] calcd for $C_{11}H_{20}Br_2N_2O_2Si$, 401.9 found 401.2.

Intermediate (1c) (69.5 g, 174 mmol, 1.0 eq) was dissolved in anhydrous THF (600 mL) and cooled to −78° C. under nitrogen. A 2.5M solution of n-butyllithium in hexanes (72.9 mL, 180 mmol, 1.05 eq) was added dropwise and the mixture was stirred at −78° C. for 10 minutes. DMF (40 mL, 520 mmol, 3.0 eq) was then added and the mixture was stirred at −78° C. for 15 minutes and was then warmed to room temperature. The reaction was quenched with water (10 mL), diluted with EtOAc (600 mL) and was washed with water (100 mL), saturated aqueous NaCl, dried over $MgSO_4$ and concentrated under reduced pressure. The recovered material was purified by silica gel chromatography (15-30% EtOAc: hexanes) to produce intermediate (1d) as a pale yellow oil (45 g).

Intermediate (1d) (105.8 g, 303 mmol, 1.0 eq) was cooled at 0° C. in ice. TFA (300 mL) was added and the mixture was stirred at 0° C. for 15 minutes, then warmed to room temperature. After 90 minutes the mixture was concentrated under reduced pressure and redissolved in EtOAc (700 mL). The organic was washed with saturated bicarbonate (2×600 mL), saturated aqueous NaCl, dried over $MgSO_4$, and concentrated under reduced pressure to produce a yellow solid. The material was suspended in hexanes (300 mL) and stirred at 0° C. for 30 minutes. The material was filtered and the solid was washed with cold hexanes (150 mL) to yield the title compound as a pale white solid (61.2 g). $^1$H-NMR (CDCl$_3$) δ (ppm): 1.4 (m, 3H), 4.5 (m, 2H), 5.2 (s, 1H), 9.2 (d, 1H).

Preparation 2

4'-Bromomethyl-3'-fluorobiphenyl-2-carboxylic Acid t-Butyl Ester

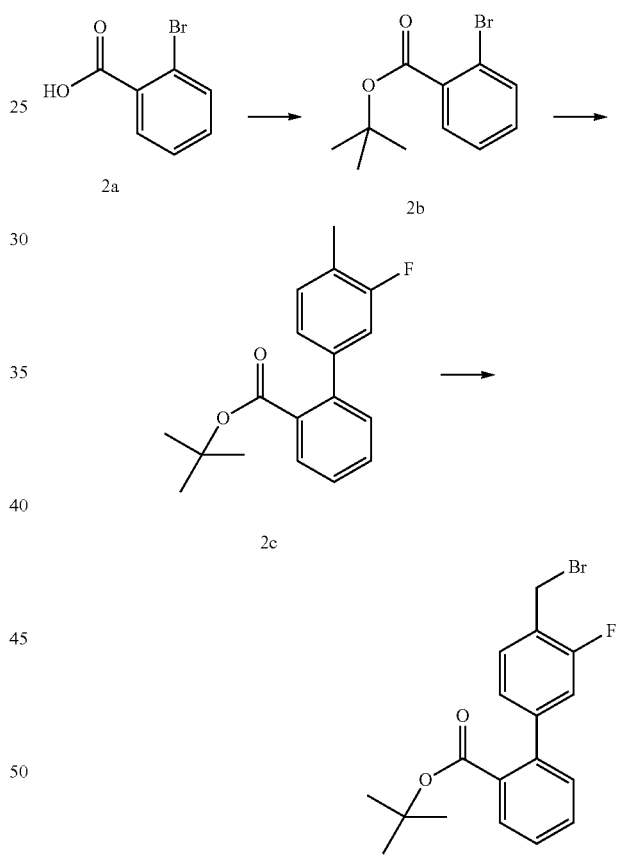

To a solution of 1.0M DCC in DCM (800 mL, 800 mol) cooled at 0° C. was added 2-bromobenzoic acid (2a) (161 g, 800 mmol) followed by DMAP (9.0 g, 740 mmol) and t-butyl alcohol (82.4 mL, 880 mmol). The mixture was stirred at room temperature for 10 minutes, then warmed to room temperature and stirred. After 16 hours, the mixture was then filtered. The organic was washed with saturated $NaHCO_3$ (400 mL), saturated aqueous NaCl, dried over $MgSO_4$, filtered and concentrated under reduced pressure to produce the crude intermediate (2b) as an oil (228.8 g).

The crude intermediate (2b) (109.6 g, 426 mmol) and 3-fluoro-4-methylphenyl-boronicacid (72.2 g, 449 mmol) were suspended in isopropyl alcohol (360 mL, 4.7 mmol). A 2.0M solution of sodium carbonate in water (360 mL, 720 mmol) was added and the mixture was degassed under nitrogen. Tetrakis(triphenylphosphine)palladium(0) (4.9 g, 4.3 mmol) was then added and the mixture was stirred at 90° C. for 46 hours. The mixture was cooled to room temperature, diluted with EtOAc (800 mL), and the layers were separated. The organic was washed with saturated aqueous NaCl and concentrated under reduced pressure. The recovered oil was purified by silica gel chromatography (3×4-6% EtOAc:hexanes) to yield intermediate (2c) as a clear oil (93.3 g).

Intermediate (2c) (89.8 g, 314 mmol, 1.0 eq) was dissolved in CCl$_4$ (620 mL, 6.4 mol) and was degassed under nitrogen. NBS (55.8 g, 314 mmol) was added, followed by benzoyl peroxide (1.5 g, 6.3 mmol) and the mixture was heated at 90° C. under nitrogen for 7 hours. The reaction was cooled in an ice bath, filtered, and concentrated under reduced pressure. The recovered oil was triturated with 150 mL of 3% EtOAc:hexanes. The solution was chilled at −20° C. for 2 hours, then filtered and washed with cold 3% EtOAc:hexanes solution (200 mL) to yield the title compound as an off white solid (88.9 g). $^1$H-NMR (CDCl$_3$) δ (ppm): 1.3 (m, 9H), 4.6 (s, 2H), 7.0-7.1 (m, 2H), 7.3 (dd, 1H), 7.4 (m, 1H), 7.5 (m, 1H), 7.8 (dd, 1H).

Preparation 3

4'-(5-Aminomethyl-2-ethoxy-4-ethylimidazol-1-ylmethyl)-3'-fluorobiphenyl-2-carboxylic Acid t-Butyl Ester 5-Bromo-2-ethoxy-3H-imidazole-4-carbaldehyde (42.0 g, 192 mmol) and 4'-bromomethyl-3'-fluorobiphenyl-2-carboxylic acid t-butyl ester (70.0 g, 192 mmol) were dissolved in DMF (890 mL, 12 mol), and the solution was cooled at 0° C. Potassium carbonate (26.5 g, 192 mmol) was slowly added and the mixture was stirred at 0° C. overnight. The reaction was then quenched with water. The mixture was extracted with EtOAc (3×300 mL), washed with saturated aqueous NaCl (500 mL), and concentrated under reduced pressure. The recovered oil was dissolved in MeOH (450 mL). Water (112 mL) was slowly added while stirring to precipitate the product. The precipitate was stirred for an additional hour before being collected by filtration. The solid was dissolved in EtOAc and concentrated under reduced pressure. The residue was allowed to stand overnight and was then stirred in 3% EtOAc:Hexane and collected by filtration. The filtrate was concentrated under reduced pressure and purified by silica gel chromatography to obtain intermediate (3a) (8.4 g).

Intermediate (3a) (54.2 g, 108 mmol) was dissolved in 1,2-dimethoxyethane (670 mL, 6.5 mol). Tetrakis(triphenylphosphine)palladium(0) (1240 mg, 1.1 mmol) was added. After 15 minutes, water (240 mL, 13 mol) and potassium carbonate (14.9 g, 108 mmol) were added and the mixture was heated at 85° C. under nitrogen. After stirring at this temperature for 10 minutes, 2,4,6-trivinylcyclotriboroxane pyridine complex (11.7 g, 48.4 mmol) was added, and the mixture was stirred for 2 hours. The mixture was then diluted with EtOAc (200 mL), washed with water and saturated aqueous NaCl, and concentrated under reduced pressure. The

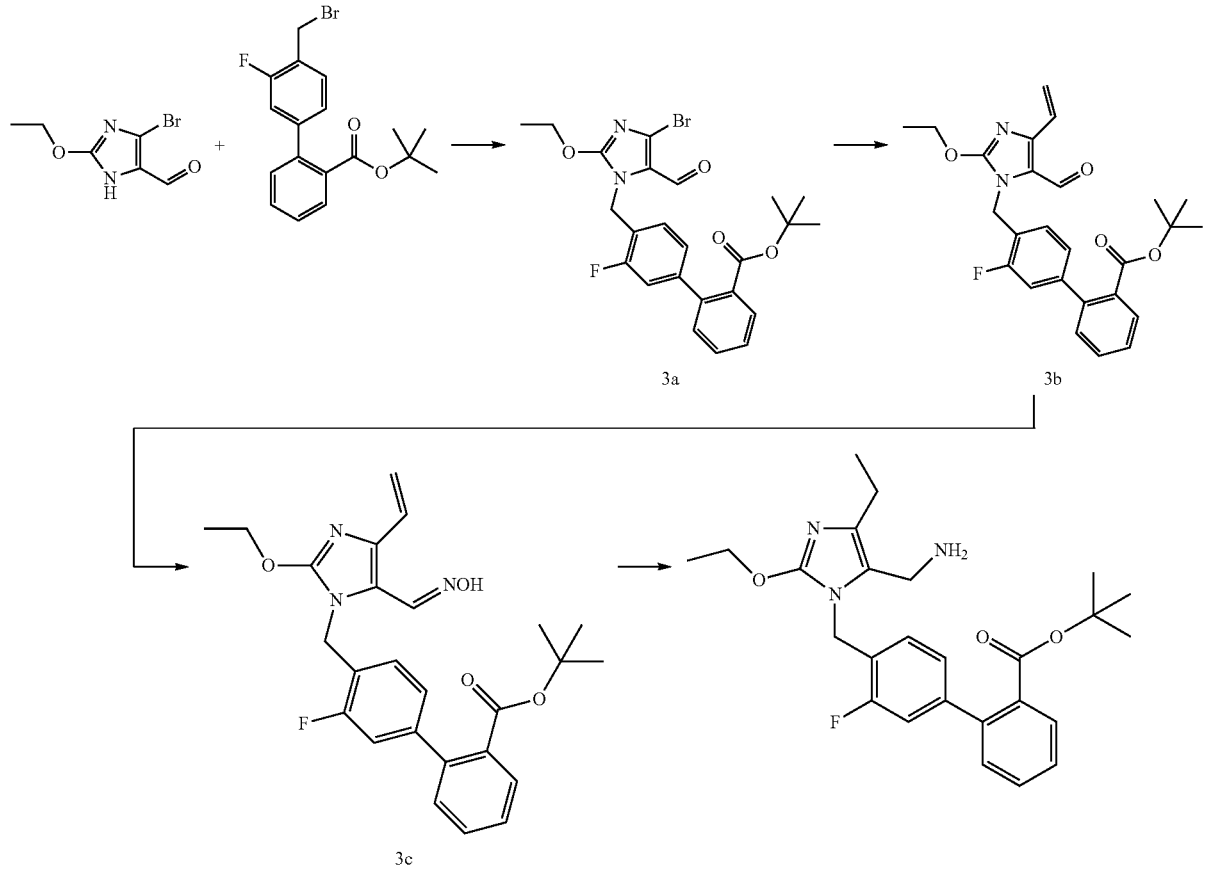

mixture was combined with a separate lot and purified by silica gel chromatography (0-50% EtOAc:hexanes) to yield intermediate (3b) (47.1 g).

Intermediate (3b) (19.0 g, 42.2 mmol) was dissolved in pyridine (250 mL, 3.1 mol). Hydroxylamine hydrochloride (8.8 g, 126 mmol) was added, followed by water (75 mL, 4.2 mol), and the mixture was stirred at room temperature overnight. Water (300 mL) was then added and the mixture was stirred for 30 minutes. The precipitant was filtered off and dried under vacuum to yield intermediate (3c) (17.3 g).

Intermediate (3c) (5.1 g, 11 mmol) was dissolved in acetic acid (100 mL, 1.8 mol) and sulfuric acid (640 µL, 12 mmol). The mixture was degassed under nitrogen and 10% Pd/C, Degussa type, wet 50% (0.05:0.45:0.5, palladium:carbon black:water, 1.5 g, 723 µmol) was added. The mixture was then degassed under hydrogen (50 psi) on a Parr shaker and shaken at room temperature. After 12 hours, the mixture was filtered and concentrated under reduced pressure. The recovered material was dissolved in EtOAc (50 mL), washed with saturated NaHCO$_3$ (50 mL) and saturated aqueous NaCl, and the liquids then evaporated. The material was purified by silica gel chromatography (0-10% MeOH:DCM) to yield the title compound as a clear oil (4.6 g, 96% purity). MS m/z: [M+H$^+$] calcd for C$_{26}$H$_{32}$FN$_3$O$_3$, 454.3; found 454.2. $^1$H NMR (CDCl$_3$) 7.82 (1H, d), 7.50 (1H, t), 7.42 (1H, t) 7.35 (1H, d), 7.27 (1H, d), 7.12 (1H, s), 7.04 (1H, d), 5.34 (1H, b), 4.65 (2H, s), 4.40 (2H, q), 4.12 (2H, q), 2.70 (1H, b), 1.50 (3H, t), 1.28 (9H, s), 1.17 (3H, t).

Preparation 4

(S)-2-Acetylsulfanyl-4-methylpentanoic Acid

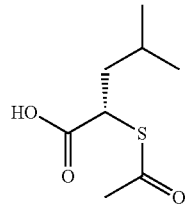

D-Leucine (8.2 g, 62.7 mmol) was dissolved in 3.0M HBr in water (99 mL, 0.3 mol) and cooled to 0° C. A solution of NaNO$_2$ (6.9 g, 100 mmol) in water (11.3 mL, 627 mmol) was slowly added over 20 minutes. The mixture was stirred at 0° C. for 3 hours and then extracted twice with ethyl ether, washed with water then saturated aqueous NaCl, dried over MgSO$_4$, filtered, and concentrated to afford (R)-2-bromo-4-methylpentanoic acid (11.5 g) as an off-yellow oil. This was taken on to the next step without further purification.

Thioacetic acid (4.2 g, 54.4 mmol) and DMF (100 mL, 1.0 mol) were combined, and the mixture cooled in an ice bath. Sodium carbonate (5.8 g, 54.4 mmol) was added. After 30 minutes, (R)-2-bromo-4-methylpentanoic acid (10.1 g, 51.8 mmol) in DMF (20 mL) was added dropwise and the mixture was stirred at 0° C. to room temperature over 6 hours. The mixture was diluted with 100 mL EtOAc and extracted with 100 mL of a 1:1 1N HCl: saturated aqueous NaCl solution. The layers were separated and the aqueous phase was extracted with additional EtOAc (100 mL). The organics were combined, washed with saturated aqueous NaCl, dried over MgSO4, filtered, and concentrated under reduced pressure. The recovered oil was dissolved into diisopropyl ether (45 mL, 320 mmol) and chilled at 0° C. Dicyclohexylamine (10.1 mL, 50.7 mmol) was added dropwise and the solid was allowed to crash out of solution. After stirring for an additional 30 minutes the material was filtered and washed with 75 mL cold diisopropyl ether. The recovered solid (14 g) was suspended in 100 mL EtOAc. 150 mL of 5% KHSO$_4$ was added and the layers were separated. The organic was washed with saturated aqueous NaCl, dried over MgSO4, filtered, and concentrated under reduced pressure. The recovered oil was then azeotroped (3×25 mL toluene) to yield the title compound (6.1 g) as a dicyclohexylamine salt.

Example 1

4'-{2-Ethoxy-4-ethyl-5-[((S)-2-mercapto-4-methyl-pentanoylamino)methyl]imidazol-1-ylmethyl}-3'-fluorobiphenyl-2-carboxylic Acid

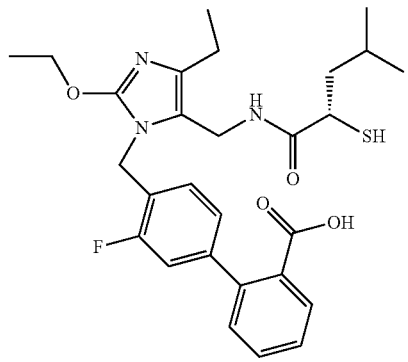 [SMILES: CCOc1nc(CC)c(CNC(=O)[C@@H](S)CC(C)C)n1Cc1ccc(-c2ccccc2C(=O)O)cc1F]

Preparation of the TFA Salt

4'-(5-Aminomethyl-2-ethoxy-4-ethylimidazol-1-ylmethyl)-3'-fluorobiphenyl-2-carboxylic acid t-butyl ester (5.0 g, 11.0 mmol), (S)-2-acetylsulfanyl-4-methylpentanoic acid (dicyclohexylamine salt; 2.1 g, 11.0 mmol), 4-methylmorpholine (1.2 mL, 11.0 mmol), and 1-hydroxy-7-azabenzotriazole (1.5 g, 11.0 mmol) were combined and dissolved in DMF (120 mL, 1.6 mol) and then cooled at 0° C. for 10 minutes. EDC (2 mL, 11.0 mmol) was added and the mixture was stirred at 0° C. for 1 hour and then at room temperature for 2 hours. The reaction was quenched with water (100 mL), the product extracted with EtOAc (100 mL), and then concentrated. The mixture was purified by column chromatography (0-50% EtOAc:hexanes) to obtain the acetylsulfanyl ester intermediate, 4'-{5-[((S)-2-acetylsulfanyl-4-methyl-pentanoylamino)methyl]-2-ethoxy-4-ethylimidazol-1-ylmethyl}-3'-fluorobiphenyl-2-carboxylic acid t-butyl ester.

This ester intermediate was dissolved in DCM:TFA (10 mL each) and the mixture was stirred at room temperature for 3 hours, and then concentrated. The residue was taken up in EtOAc, washed with a saturated NaHCO$_3$ solution, dried over MgSO$_4$, and concentrated to yield 5.3 g of the acetylsulfanyl acid intermediate, 4'-{5-[((S)-2-acetylsulfanyl-4-methylpentanoylamino)methyl]-2-ethoxy-4-ethylimidazol-1-ylmethyl}-3'-fluorobiphenyl-2-carboxylic acid.

This acid intermediate was dissolved in MeOH (30 mL). The solution was degassed, stirred under nitrogen, and cooled at 0° C. 0.5M NaOMe in MeOH (25 mL, 2 eq.) was added and the mixture was stirred at 0° C. under nitrogen for 20 minutes. The mixture was then acidified with 1N HCl (15 mL). The mixture was concentrated, dissolved in EtOAc, washed with water, dried over MgSO₄, filtered, and then concentrated. The product was purified by preparative HPLC 10-70% MeCN:water with 0.5% TFA (70 minute method) to yield 2.3 g of the TFA salt.

Preparation of the HCl Salt

Amberlite IRA-900 resin (80 g, Aldrich) was suspended in 1M HCl (600 mL). The mixture was shaken occasionally over 60 minutes. The bulk of the supernatant was decanted to afford wet resins, which were then transferred to a 100 mL plastic column. The column was washed by elution with water (200 mL) and 50% aq. MeCN (200 mL) until the pH of the passed eluant was ~5. The TFA salt of 4'-{2-ethoxy-4-ethyl-5-[((S)-2-mercapto-4-methylpentanoyl-amino)methyl]imidazol-1-ylmethyl}-3'-fluorobiphenyl-2-carboxylic acid (2.3 g, 3.5 mmol) was dissolved in 50% aq. MeCN (8 mL), and loaded onto the prepared column. The compound was eluted with 50% aq. MeCN under gravity. Fractions were collected in 5 mL volumes, and analyzed by HPLC. Fractions having the desired mass were combined and lyophilized, affording the title compound as a HCl salt (1.5 g, 97% purity).

Preparation of the Title Compound

This HCl salt was dissolved in MeOH (5 mL) and water (5 mL), and the mixture had a pH 2.2. The material was slowly brought up to a pH of 4.2 with a series of 100 µL injections of 1 N NaOH, then adjusted with 1N HCl (25 µL), NaOH (2×25 µL), then HCl (25 µL) to arrive at the isoelectric point. The solution was observed to be cloudy. Material was oiling out. EtOAc (20 mL) was added to extract the solid, which was then removed from the aqueous layer and concentrated to yield the title compound (1.3 g, 98% purity). Analysis of the ion content of this material using ion chromatography gave: 0.06% Na, 0.1% Cl, and <0.1% TFA (w/w).

Example 2

Crystalline Freebase of 4'-{2-Ethoxy-4-ethyl-5-[((S)-2-mercapto-4-methylpentanoylamino)methyl]imidazol-1-ylmethyl}-3'-fluorobiphenyl-2-carboxylic Acid 4'-{2-Ethoxy-4-ethyl-5-[((S)-2-mercapto-4-methylpentanoylamino)methyl]-imidazol-1-ylmethyl}-3'-fluorobiphenyl-2-carboxylic acid, prepared as described in Example 1, was determined to be non-crystalline by powder X-ray diffraction.

This amorphous form (35.7 mg) was added to acetone (1 mL) to yield a solution of about 36 mg/mL. The solution was heated to 35-40° C. for about 30 minutes, then gradually cooled to room temperature. The solution was then refrigerated (4° C.) for approximately 44 hours. Precipitates were observed and the volume was reduced by half under a gentle stream of nitrogen at room temperature. The solids were isolated and dried under nitrogen to yield the title crystalline compound (22.3 mg). The crystalline nature of the product was verified by XRPD pattern, DSC thermograph, and TGA trace analysis.

Example 3

Powder X-Ray Diffraction

Powder X-ray diffraction patterns were obtained with a Rigaku Miniflex PXRD diffractometer using Cu Kα (30.0 kV, 15.0 mA) radiation. The analysis was performed with the goniometer running in continuous-scan mode of 2° (2θ) per min with a step size of 0.03° over a range of 2 to 40° in two-theta angle. Samples were prepared on quartz specimen holders as a thin layer of powdered material. The instrument was calibrated with a silicon metal standard, within ±0.02° two-theta angle. A representative PXRD pattern for a sample of the crystalline form of Example 2 is shown in FIG. 1.

The numerous intense powder diffraction peaks and relatively flat baseline depicted in FIG. 1 strongly indicated that the crystalline form of Example 2 possessed good crystallinity. Quite the contrary, the amorphous compound of Example 1, the starting material prior to crystallization, did not show any diffraction peaks.

Example 4

Thermal Analysis

Differential scanning calorimetry (DSC) was performed using a TA Instruments Model Q-100 module with a Thermal Analyst controller. Data were collected and analyzed using TA Instruments Thermal Solutions software. A 1.64 mg sample of the crystalline form of Example 2 was accurately weighed into a covered aluminum pan. After a 5 minute isothermal equilibration period at 22° C., the sample was heated using a linear heating ramp of 10° C./min from 22° C. to 250° C. A representative DSC thermograph is shown in FIG. 2.

The DSC thermograph demonstrates that the crystalline compound of the invention has excellent thermal stability with a melting point at about 144° C. and no thermal decomposition below 150° C. The non-complex thermal profile does not show any undesired endothermic or exothermic peak prior to the melting endotherm at 144° C., which suggests that this crystalline solid is most likely an anhydrous crystalline form.

A representative TGA trace is shown in FIG. 3, and indicates that a sample of the crystalline form of Example 2 lost a small amount (about 1.8%) of weight from room temperature to 200° C., which is consistent with the loss of residual moisture or solvent.

Example 5

Dynamic Moisture Sorption Assessment

A dynamic moisture sorption (DMS) assessment (also known as a moisture sorption-desorption profile) was performed for a sample of the crystalline form of Example 2 using a VTI atmospheric microbalance, SGA-100 system (VTI Corp., Hialeah, Fla. 33016). A sample size of approximately 4.27 mg was used and the humidity was set at the ambient value at the start of the analysis. The DMS analysis consisted of a scan rate of 5% RH/step over the full humidity range of 2% relative humidity (RH) to 90% RH. The DMS run was performed isothermally at 25° C. A representative DMS profile is shown in FIG. 4.

The DMS profile demonstrates that the crystalline compound of the invention has a reversible sorption/desorption profile with insignificant hygroscopicity. The crystalline compound has a small weight gain when it exposed to a broad humidity range from 2% RH up to 90% RH, and less than about 1% weight gain when exposed to up to 75% RH, which indicates that the crystalline form possesses only a minimal risk of hygroscopicity at ambient conditions.

Example 6

Crystalline Freebase of 4'-{2-Ethoxy-4-ethyl-5-[((S)-2-mercapto-4-methylpentanoylamino)methyl]imidazol-1-ylmethyl}-3'-fluorobiphenyl-2-carboxylic Acid The title crystalline compound was prepared in a manner similar to that described in Example 2, but using MeCN in place of acetone:

Amorphous 4'-{2-ethoxy-4-ethyl-5-[((S)-2-mercapto-4-methylpentanoylamino)-methyl]imidazol-1-ylmethyl}-3'-fluorobiphenyl-2-carboxylic acid (98.8 mg) was added to MeCN (4 mL) to yield a solution of about 24.7 mg/mL. The solution was heated to 35° C. for about 30 minutes, then gradually cooled to room temperature. The solution was then refrigerated (4° C.) for approximately 42 hours. Precipitates were observed and the volume was reduced by half under a gentle stream of nitrogen at room temperature. The solids were isolated and dried under nitrogen to yield the title crystalline compound (73.8 mg).

The same crystalline material was obtained as in Example 2, as evidenced by a similar PXRD pattern, DSC thermograph, and TGA trace. However, this material exhibited improved crystallinity properties compared with the material of Example 2, as evidenced by the slightly higher melting point of about 151° C.

Preparation 5

Crystalline Freebase 4'-(5-Aminomethyl-2-ethoxy-4-ethylimidazol-1-ylmethyl)-3'-fluorobiphenyl-2-carboxylic Acid t-Butyl Ester

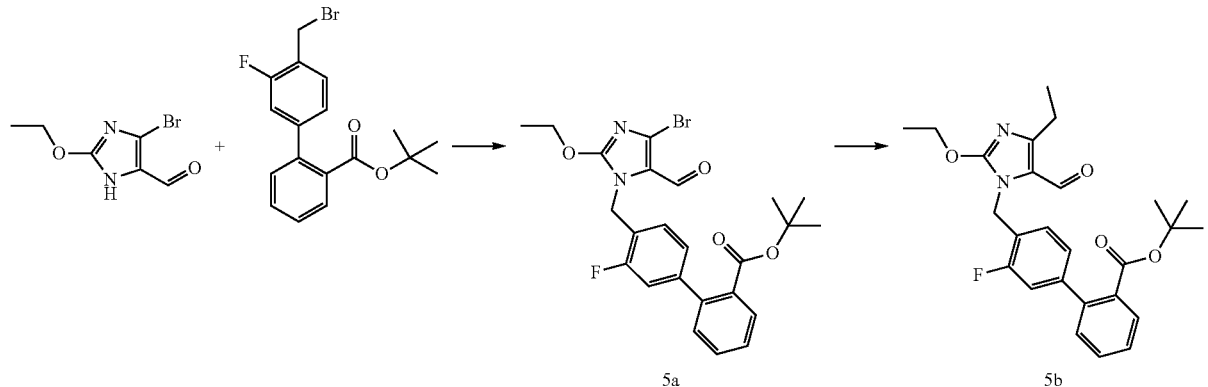

5a

5b

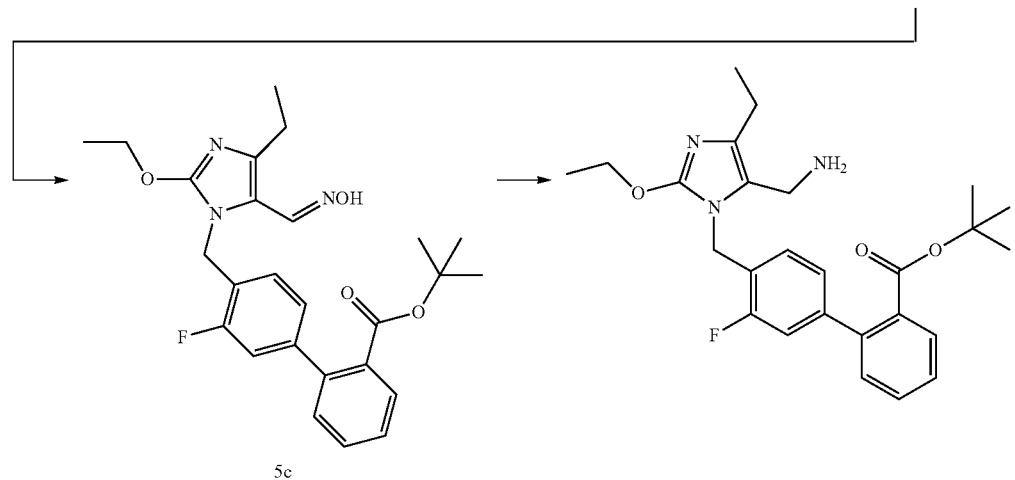

5c

5-Bromo-2-ethoxy-3H-imidazole-4-carbaldehyde (22.0 g, 100 mmol, 1.1 eq.), 4'-bromomethyl-3'-fluorobiphenyl-2-carboxylic acid t-butyl ester (33.0 g, 90 mmol, 1 eq.), and Bu₄NBr (1.6 g, 5 mmol, 0.05 eq.) were dissolved in toluene (400 mL) and 1N NaOH (120 mL, 120 mmol, 1.2 eq.). The resulting mixture was stirred at 27° C. for 48-60 hours. The toluene layer was separated, washed with water (2×200 mL), then removed by distillation. EtOH (350 mL) was added to the residue and the mixture was heated to 50-60° C. until the solids dissolved. The mixture was cooled to room temperature over 4 hours, then cooled to 4° C. and stirred at 4° C. for 4 hours. The solids were filtered off, washed with cold EtOH (60 mL) and dried at room temperature under vacuum for 24 hours to yield intermediate (5a) (~39 g).

Intermediate (5a) (20.0 g, 40 mmol, 1 eq.), potassium ethyl trifluoroborate (7.1 g, 52 mmol, 1.3 eq.), palladium(II) acetate (224 mg, 1 mmol, 0.025 eq.), cataCXium® A (butyldi-1-adamantylphosphine; CAS#321921-71-5; 538 mg, 1.45 mmol, 0.04 eq.), and Cs₂CO₃ (45 g, 138 mmol, 3.45 eq.) were dissolved in toluene (240 mL) and water (80 mL). The mixture was flushed with nitrogen (3×) under vacuum, then heated to 90° C. for 16 hours. The mixture was then cooled to room temperature and the layers were separated. The organic layer was washed with water (2×200 mL) then distilled under reduced pressure to yield an oil. The oil was dissolved in EtOH (240 mL). Water (80 mL) was added and the mixture was stirred for 30 minutes. The mixture was filtered to remove solids, the solids were washed with 75% EtOH (130 mL), and the filtrate collected to yield intermediate (5b) in an EtOH solution, which was used directly in the next step.

The EtOH solution of intermediate (5b) (10 mmol, 1 eq.) was combined with hydroxylamine hydrochloride (27.2 g, 52 mmol, 1.3 eq.) and NaHCO₃ (35.2 g, 3.45 eq.). The mixture was stirred at 40° C. for 24 hours, then cooled to room temperature. The precipitant was filtered off, washed with 75% EtOH (100 mL) and 50% EtOH (200 mL), then dried under reduced pressure at 30° C. for 24 hours to yield intermediate (5c) (15 g).

Intermediate (5c) (5 g) was combined with EtOH (100 mL), NH₄OH (28%, 6 mL), and Raney Ni (wet 10 g) to form a slurry. The mixture was degassed under nitrogen (3×), degassed under hydrogen (3×), then stirred under hydrogen (1 atm) for 3 hours. The mixture was filtered to remove the catalyst and the solids were washed with EtOH (20 mL). The filtrate was then treated with charcoal (0.5 g) and filtered again. The filtrate was then distilled under vacuum to yield an oil. Heptanes were added (50 mL) and the mixture distilled to an oil (2×). The remaining oil was dissolved in heptanes (60 mL) by heating the mixture and stirring at 4° C. for 24 hours. The solids were then filtered, washed with cold heptanes (10 mL), and dried at room temperature for 24 hours to yield the title compound as a crystalline material (3.8 g).

Preparation 6

Crystalline Freebase 4'-{5-[((S)-2-Acetylsulfanyl-4-methylpentanoylamino)methyl]-2-ethoxy-4-ethylimidazol-1-ylmethyl}-3'-fluorobiphenyl-2-carboxylic Acid

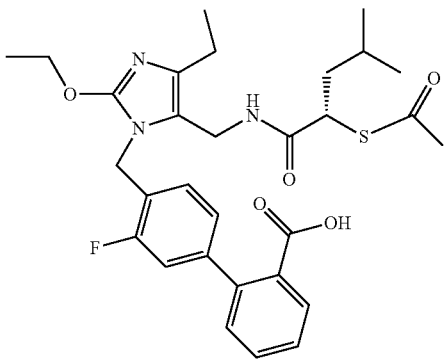 [SMILES: CCOc1nc(CC)c(CNC(=O)[C@H](CC(C)C)SC(C)=O)n1Cc1ccc(-c2ccccc2C(=O)O)cc1F]

Crystalline 4'-(5-aminomethyl-2-ethoxy-4-ethylimidazol-1-ylmethyl)-3'-fluorobiphenyl-2-carboxylic acid t-butyl ester (dicyclohexylamine salt; 18 g, 40 mmol, 1 eq.), (S)-2-acetylsulfanyl-4-methylpentanoic acid (18 g, 48 mmol, 1.2 eq.), and HCTU (19 g, 48 mmol, 1.2 eq.) were combined in a pre-chilled vessel (0° C. for 10 minutes) and cold DCM (240 mL) was added. The mixture was stirred at 1±2° C. for 5-15 hours. 4% NaHCO₃ (200 mL) was added and the mixture was stirred for 15 minutes. The DCM layer was separated and distilled to ~100 mL. IPAc (150 mL) was added and distill to 150 mL. Additional IPAc (200 mL) was added and the mixture was washed with 4% NaHCO₃ (2×200 mL) and water (200 mL). The solution was stirred with 15% NH₄Cl (300 mL) for 15 minutes, the pH was adjusted to 5.5 with 1N HCl, and then stirred for 1 hour. The solids were filtered off. The filtrate was washed with IPAc (50 mL), and the IPAc layer separated. The IPAc layer was stirred with 15% NH₄Cl (200 mL) for 3 hours and any solids filtered off The filtrate was washed with saturated aqueous NaCl (150 mL) and distilled under vacuum to ~60 mL. DCM (50 mL) was added and distilled off DCM (200 mL) was added and the mixture was cooled 0-5° C. TFA (70 mL) was added slowly (slightly exothermic) at below 15° C., and the mixture was stirred at 20° C. for 16 hours. The mixture was concentrated to ~150 ml, and IPAc (150 mL) was added. The mixture was distilled to ~150 mL. Additional IPAc (150 mL) was added, and again distilled to ~150 mL. IPAc (200 mL) was added and the resulting solution was slowly added to pre-cooled K₂CO₃ (52 g) in water (250 mL) at below 10° C. (mildly exothermic, pH>7 must >6 during quench) over 15 minutes. The pH was monitored during the transfer, and additional base (8 g) was added when the pH dropped below 6. The IPAc layer was separated and washed with saturated aqueous NaCl (150 mL). The IPAc solution was distilled to ~50 mL. MTBE (100 mL) was added and the mixture distilled to ~50 mL. Additional MTBE (100 mL) was added and the mixture was stirred at room temperature for 3 hours, forming a slurry, which was then stirred at 4° C. for 16 hours. The solids were filtered off and washed with MTBE/diisopropyl ether (1:1; 100 mL). The solids were then dried at room temperature for 60 hours under nitrogen to yield the title compound as a crystalline material (18.2 g).

Example 7

Crystalline Freebase of 4'-{2-Ethoxy-4-ethyl-5-[((S)-2-mercapto-4-methylpentanoylamino)methyl]imidazol-1-ylmethyl}-3'-fluorobiphenyl-2-carboxylic Acid Crystalline 4'-{5-[((S)-2-acetylsulfanyl-4-methylpentanoylamino)methyl]-2-ethoxy-4-ethylimidazol-1-ylmethyl}-3'-fluorobiphenyl-2-carboxylic acid (2.3 g, 4 mmol, 1 eq.) and DTT (62 mg, 0.4 mmol, 0.1 eq.) was dissolved in MeOH (30 mL). The resulting solution was degassed with nitrogen (3 times) and cooled at 0° C. NaOMe (25% in MeOH, 1.7 mL) was added and the mixture was stirred at 0° C. for 30 minutes. AcOH (3 g, 50 mmol, 4 eq.) was added to quench the reaction at 0° C. The mixture was warmed to 20° C. Deionized water (10 mL) was added slowly. The mixture was stirred at 20° C. for 3 hours and then stirred at 4° C. for 1 hour until precipitates were formed. The solids were filtered and washed with MeOH/$H_2O$ (2:1; 30 mL), then dried under nitrogen at 20° C. for 48 hours to yield the title crystalline compound (1.2 g).

The same material was obtained as in Example 2, as evidenced by a similar PXRD pattern, DSC thermograph, and TGA trace.

Example 8

Thermal Stability

A sample of the crystalline form prepared as in Example 6 was heated at 60° C. for 5 days. The sample lost only 2% of its purity, thus the crystalline compound of the invention has excellent thermal stability. On the other hand, a sample of the amorphous compound of Example 1 lost about 50% of its purity after being heated at 60° C. for 1 day.

Example 9

Micronization

A sample of the crystalline freebase prepared as in Example 7 was micronized with a jet mill to give a free-flowing white powder. No issues were encountered during the micronization process. Particle size distribution was as follows:

|  | Pre-Micronization | Post- Micronization |
|---|---|---|
| D (v, 0.9) | 50.73 μm | 7.07 μm |
| D (v, 0.5) | 11.32 μm | 2.59 μm |
| D (v, 0.1) | 1.73 μm | 0.79 μm |

No significant changes were observed in the powder x-ray diffraction pattern, TGA, DSC, DMS, chemical purity, chiral purity and moisture content for the micronized material compared to the unmicronized material. For example, as noted in Example 5, a representative DMS trace for a sample of the crystalline freebase of Example 2 showed less than 1% weight gain in the humidity range of 40-75% RH, while the micronized crystalline freebase prepared as in Example 7 showed a 0.7% weight gain in this humidity range.

Example 10

Infrared Analysis

The infrared (IR) absorption spectrum was determined over the frequency range 4000 to 675 $cm^{-1}$ using an Avatar 360 FT-IR spectrometer equipped with a Nicolet attenuated total reflection (ATR) sample holder. A representative IR absorption spectrum for a sample of the crystalline freebase prepared as in Example 6 is shown in FIG. 5, and the peak list is provided below.

| Position | Intensity |
|---|---|
| 694.9 | 88.819 |
| 758.6 | 67.649 |
| 799.4 | 84.900 |
| 869.2 | 88.068 |
| 897.6 | 88.599 |
| 1062.3 | 79.779 |
| 1106.9 | 89.114 |
| 1132.9 | 74.282 |
| 1172.6 | 79.946 |
| 1198.4 | 78.901 |
| 1253.9 | 64.801 |
| 1357.1 | 68.642 |
| 1407.6 | 70.163 |
| 1430.2 | 66.601 |
| 1460.1 | 66.434 |
| 1482.5 | 59.454 |
| 1500.0 | 55.792 |
| 1550.9 | 55.792 |
| 1642.8 | 54.005 |
| 1709.1 | 62.016 |
| 1943.8 | 82.854 |
| 2526.7 | 78.079 |
| 2871.6 | 76.953 |
| 2957.6 | 68.117 |
| 3323.5 | 87.685 |

The significant absorption bands were observed at 3324±1, 2958±1, 2872±1, 2527±1, 1709±1, 1643±1, 1551±1, 1500±1, 1357±1, 1254±1, 1133±1, 1062±1, 869±1, 799±1, 759±1, and 695±1 $cm^{-1}$.

Example 11

Solid State Stability Assessment

Samples of the crystalline freebase prepared as in Example 7, about 100 mg each, were stored in multiple vials at 5° C. (closed container), 25° C. (closed container), and at 40° C. (closed container). At specific intervals, the entire contents of a representative vial was analyzed by the following HPLC method:

Column: Agilent Zorbox SB-C18, 4.6×250 mm, 5 μm (Part No. 880975-902). Mobile Phase A: 80% $H_2O$, 20% MeCN, 0.01% TFA. Mobile Phase B: 80% MeCN, 20% $H_2O$, 0.01% TFA. Flow rate: 1 mL/min. Injection Volume: 20 μL. Detector: 250 nm.

Samples were prepared as 0.2-0.5 mg/mL stock solutions in 100% MeCN, depending on the solubility, for injection onto the HPLC.

The purity of the samples was determined by HPLC area percentage (% AUC). After 28 days of storage, for the crystalline freebase samples kept under all conditions, there was no detectable change in chemical purity, and no observable change in the appearance of the material.

For example, as shown below, after 28 days of storage at 40° C., there was no detectable change in chemical purity of the crystalline freebase, while the amorphous freebase and the TFA salt (both prepared as described in Example 1) did show a decline in purity.

| Material | purity at time 0 | purity after 7 days at 40° C. | purity after 14 days at 40° C. | purity after 28 days at 40° C. |
|---|---|---|---|---|
| crystalline freebase | 98.5 | 98.4 | 98.3 | 98.4 |
| amorphous freebase | 97.5 | 86.8 | 82.4 | n.d. |
| amorphous TFA salt | 97.7 | 73.5 | 62.2 | 47.1 | n.d. = not measured for this sample

Assay 1

$AT_1$ and $AT_2$ Radioligand Binding Assays

These in vitro assays were used to assess the ability of test compounds to bind to the $AT_1$ and the $AT_2$ receptors.

Membrane Preparation From Cells Expressing Human $AT_1$ or $AT_2$ Receptors

Chinese hamster ovary (CHO-K1) derived cell lines stably expressing the cloned human $AT_1$ or $AT_2$ receptors, respectively, were grown in HAM's-F12 medium supplemented with 10% fetal bovine serum, 10 µg/ml penicillin/streptomycin, and 500 µg/ml geneticin in a 5% $CO_2$ humidified incubator at 37° C. $AT_2$ receptor expressing cells were grown in the additional presence of 100 nM PD123,319 ($AT_2$ antagonist). When cultures reached 80-95% confluence, the cells were washed thoroughly in PBS and lifted with 5 mM EDTA. Cells were pelleted by centrifugation and snap frozen in MeOH-dry ice and stored at −80° C. until further use.

For membrane preparation, cell pellets were resuspended in lysis buffer (25 mM Tris/HCl pH 7.5 at 4° C., 1 mM EDTA, and one tablet of Complete Protease Inhibitor Cocktail Tablets with 2 mM EDTA per 50 mL buffer (Roche cat.#1697498, Roche Molecular Biochemicals, Indianapolis, Ind.)) and homogenized using a tight-fitting Dounce glass homogenizer (10 strokes) on ice. The homogenate was centrifuged at 1000×g, the supernatant was collected and centrifuged at 20,000×g. The final pellet was resuspended in membrane buffer (75 mM Tris/HCl pH 7.5, 12.5 mM $MgCl_2$, 0.3 mM EDTA, 1 mM EGTA, 250 mM sucrose at 4° C.) and homogenized by extrusion through a 20G gauge needle. Protein concentration of the membrane suspension was determined by the method described in Bradford (1976) *Anal Biochem.* 72:248-54. Membranes were snap frozen in MeOH-dry ice and stored at −80° C. until further use.

Ligand Binding Assay to Determine Compound Affinities for the Human $AT_1$ and $AT_2$ Angiotensin Receptors Binding assays were performed in 96-well Acrowell filter plates (Pall Inc., cat.#5020) in a total assay volume of 100 with 0.2 µg membrane protein for membranes containing the human $AT_1$ receptor, or 2 µg membrane protein for membranes containing the human $AT_2$ receptor in assay buffer (50 mM Tris/HCl pH 7.5 at 20° C., 5 mM $MgCl_2$, 25 µM EDTA, 0.025% BSA). Saturation binding studies for determination of $K_d$ values of the ligand were done using N-terminally Europium-labeled angiotensin-II ([Eu]AngII, H—(Eu—$N^1$)-Ahx-Asp-Arg-Val-Tyr-Ile-His-Pro-Phe-OH; PerkinElmer, Boston, Mass.) at 8 different concentrations ranging from 0.1 nM to 30 nM. Displacement assays for determination of $pK_i$ values of test compounds were done with [Eu]AngII at 2 nM and 11 different concentrations of drug ranging from 1 pM to 10 µM. Drugs were dissolved to a concentration of 1 mM in DMSO and from there serially diluted into assay buffer. Nonspecific binding was determined in the presence of 10 µM unlabeled angiotensin-II. Assays were incubated for 120 minutes in the dark, at room temperature or 37° C., and binding reactions were terminated by rapid filtration through the Acrowell filter plates followed by three washes with 200 µL ice cold wash buffer (50 mM Tris/HCl pH 7.5 at 4° C., 5 mM $MgCl_2$) using a Waters filtration manifold. Plates were tapped dry and incubated with 50 µl DELFIA Enhancement Solution (PerkinElmer cat.#4001-0010) at room temperature for 5 minutes on a shaker. Filter-bound [Eu]AngII was quantitated immediately on a Fusion plate reader (PerkinElmer) using Time Resolved Fluorescence (TRF). Binding data were analyzed by nonlinear regression analysis with the GraphPad Prism Software package (GraphPad Software, Inc., San Diego, Calif.) using the 3-parameter model for one-site competition. The BOTTOM (curve minimum) was fixed to the value for nonspecific binding, as determined in the presence of 10 µM angiotensin II. $K_i$ values for drugs were calculated from observed $IC_{50}$ values and the $K_d$ value of [Eu]AngII according to the Cheng-Prusoff equation described in Cheng et al. (1973) *Biochem Pharmacol.* 22(23):3099-108. Selectivities of test compounds for the $AT_1$ receptor over the $AT_2$ receptor were calculated as the ratio of $AT_2K_i/AT_1K_i$. Binding affinities of test compounds were expressed as negative decadic logarithms of the $K_i$ values ($pK_i$).

In this assay, a higher $pK_i$ value indicates that the test compound has a higher binding affinity for the receptor tested. The compound of Example 1 was found to have a $pK_i$ value greater than about 7.0.

Assay 2

In Vitro Assays for the Quantitation of Inhibitor Potencies ($IC_{50}$) at Human and Rat NEP, and Human ACE The inhibitory activities of compounds at human and rat NEP and human angiotensin converting enzyme (ACE) were determined using in vitro assays as described below.

Extraction of NEP Activity, from Rat Kidneys

Rat NEP was prepared from the kidneys of adult Sprague Dawley rats. Whole kidneys were washed in cold PBS and brought up in ice-cold lysis buffer (1% Triton X-114, 150 mM NaCl, 50 mM Tris pH 7.5; Bordier (1981) *J. Biol. Chem.* 256: 1604-1607) in a ratio of 5 mL of buffer for every gram of kidney. Samples were homogenized using a polytron hand held tissue grinder on ice. Homogenates were centrifuged at 1000×g in a swinging bucket rotor for 5 minutes at 3° C. The pellet was resuspended in 20 mL of ice cold lysis buffer and incubated on ice for 30 minutes. Samples (15-20 mL) were then layered onto 25 mL of ice-cold cushion buffer (6% w/v sucrose, 50 mM pH 7.5 Tris, 150 mM NaCl, 0.06%, Triton X-114), heated to 37° C. for 3-5 minutes and centrifuged at 1000×g in a swinging bucket rotor at room temperature for 3 minutes. The two upper layers were aspirated off, leaving a viscous oily precipitate containing the enriched membrane fraction. Glycerol was added to a concentration of 50% and samples were stored at −20° C. Protein concentrations were quantitated using a BCA detection system with BSA as a standard.

Enzyme Inhibition Assays

Recombinant human NEP and recombinant human ACE were obtained commercially (R&D Systems, Minneapolis, Minn., catalog numbers 1182-ZN and 929-ZN, respectively). The fluorogenic peptide substrate Mca-BK2 (Mca-Arg-Pro-Pro-Gly-Phe-Ser-Ala-Phe-Lys(Dnp)-OH; Johnson et al. (2000) *Anal. Biochem.* 286: 112-118) was used for the human NEP and ACE assays, and Mca-RRL (Mca-DArg-Arg-Leu-(Dnp)-OH; Medeiros et al. (1997) *Braz. J. Med. Biol. Res.* 30:1157-1162) was used for the rat NEP assay (both from Anaspec, San Jose, Calif.).

Test compounds were diluted to 12 concentrations from 10 μM to 20 pM in Assay

Buffer. Assays were started by adding 25 μL of enzyme to 12.5 μL of test compound at each of the 12 concentrations. Test compounds were allowed to equilibrate with the enzyme for 10 minutes before 12.5 μL of the fluorogenic substrates were added to initiate the reaction. Reactions were terminated by the addition of 10 μL of 3.6% glacial acetic acid after 20 minutes of incubation.

For sulfhydryl-containing test compounds, the test compounds may be diluted in Assay Buffer containing a 400 μM concentration of tris(2-carboxyethyl)phosphine hydrochloride (Thermo Scientific, Rockford, Ill.) (TCEP). The test compounds are then allowed to reduce for 40 minutes at room temperature before adding the enzyme. Test compounds are then allowed to equilibrate with the enzyme for 20 minutes before adding the fluorogenic substrates. Reactions are terminated as above.

Plates were read on a fluorometer with excitation and emission wavelengths set to 320 nm and 405 nm, respectively. Raw data (relative fluorescence units) were normalized to % activity from the average high readings (no inhibition, 100% enzyme activity) and average low readings (full inhibition, highest inhibitor concentration, 0% enzyme activity) using three standard NEP and ACE inhibitors, respectively. Non-linear regression of the normalized data was performed using a one site competition model (GraphPad Software, Inc., San Diego, Calif.). Data were reported as $pIC_{50}$ values. The compound of Example 1 was found to have a $pIC_{50}$ value greater than or equal to about 7.0.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A method for suppressing or alleviating the symptoms of chronic heart failure, comprising administering to a patient having chronic heart failure a therapeutically effective amount of a crystalline freebase of 4'-{2-ethoxy-4-ethyl-5-[((S)-2-mercapto-4-methylpentanoylamino)methyl]imidazol-1-ylmethyl}-3'-fluorobiphenyl-2-carboxylic acid, characterized by a powder x-ray diffraction pattern comprising diffraction peaks at 2θ values of 6.66±0.20, 9.8±0.20, and 18.12±0.20.

2. The method of claim 1, wherein the crystalline freebase is characterized by having one or more additional diffraction peaks at 2θ values selected from 12.68±0.20, 13.54±0.20, 15.02±0.20, 19.32±0.20, 21.20±0.20, 22.62±0.20, 24.56±0.20, 25.30±0.20, 25.96±0.20, and 27.32±0.20.

3. The method of claim 1, wherein the crystalline freebase is characterized by a powder x-ray diffraction pattern in which the peak positions are substantially in accordance with the peak positions of the pattern shown in FIG. 1.

4. The method of claim 1, wherein the crystalline freebase is characterized by a differential scanning calorimetry trace which has a melting point in the range of about 144° C. to about 148° C.

5. The method of claim 1, wherein the crystalline freebase is characterized by a differential scanning calorimetry trace substantially in accordance with that shown in FIG. 2.

6. The method of claim 1, wherein the crystalline freebase is characterized by an infrared absorption spectrum with significant absorption bands at 3324±1, 2958±1, 2872±1, 2527±1, 1709±1, 1643±1, 1551±1, 1500±1, 1357±1, 1254±1, 1133±1, 1062±1, 869±1, 799±1, 759±1, and 695±1 cm$^{-1}$.

* * * * *